US008697350B2

(12) United States Patent
Ruegg et al.

(10) Patent No.: US 8,697,350 B2
(45) Date of Patent: Apr. 15, 2014

(54) BIOMARKER COMBINATIONS FOR COLORECTAL CANCER

(75) Inventors: Curzio Ruegg, Lausanne (CH); Sylvain Monnier-Benoit, Malbuison (FR); Laura Ciarloni, Epalinges (CH); Stavros Therianos, Lausanne (CH)

(73) Assignee: Diagnoplex, Epalinges (CH)

( * ) Notice: Subject to any disclaimer, the term of this patent is extended or adjusted under 35 U.S.C. 154(b) by 759 days.

(21) Appl. No.: 12/451,869

(22) PCT Filed: Jun. 4, 2008

(86) PCT No.: PCT/IB2008/003175
§ 371 (c)(1),
(2), (4) Date: Aug. 12, 2010

(87) PCT Pub. No.: WO2009/037572
PCT Pub. Date: Mar. 26, 2009

(65) Prior Publication Data
US 2010/0330079 A1     Dec. 30, 2010

Related U.S. Application Data

(60) Provisional application No. 60/933,272, filed on Jun. 4, 2007.

(51) Int. Cl.
*C12Q 1/00*     (2006.01)
*C12Q 1/68*     (2006.01)

(52) U.S. Cl.
USPC .......................... 435/4; 435/6.1; 435/6.14

(58) Field of Classification Search
None
See application file for complete search history.

(56) References Cited

U.S. PATENT DOCUMENTS

| | | | |
|---|---|---|---|
| 4,230,797 A | 10/1980 | Boguslaski et al. | 435/7.23 |
| 4,233,402 A | 11/1980 | Maggio et al. | 435/5 |
| 4,275,149 A | 6/1981 | Litman et al. | 435/7.91 |
| 4,376,110 A | 3/1983 | David et al. | 435/5 |
| 4,659,678 A | 4/1987 | Forrest et al. | 436/512 |
| 4,727,022 A | 2/1988 | Skold et al. | 435/7.2 |
| 5,072,011 A | 12/1991 | Abrams et al. | 556/137 |
| 5,244,919 A | 9/1993 | Abrams et al. | 514/492 |
| 5,744,305 A | 4/1998 | Fodor et al. | 506/16 |
| 6,455,668 B1 | 9/2002 | Mack et al. | 530/300 |
| 6,894,049 B1 | 5/2005 | Wong et al. | 514/52.1 |
| 2004/0265824 A1 | 12/2004 | Buckhaults et al. | 435/6 |
| 2005/0089862 A1 | 4/2005 | Therianos et al. | 435/6 |
| 2007/0202496 A1* | 8/2007 | Beretta | 435/5 |

FOREIGN PATENT DOCUMENTS

| | | |
|---|---|---|
| EP | 1 564 302 | 8/2005 |
| WO | WO 00/71577 | 11/2000 |
| WO | WO 03/048377 | 6/2003 |
| WO | WO 2004/056456 | 7/2004 |
| WO | WO 2004/088309 | 10/2004 |
| WO | WO 2006/015742 | 2/2006 |
| WO | WO 2006/039405 | 4/2006 |
| WO | WO-2007048074 A1 | 4/2007 |
| WO | WO 2007/073220 A1 * | 6/2007 ............. G01N 33/50 |
| WO | WO 2009/037572 | 3/2009 |

OTHER PUBLICATIONS

Zhang et al. (Oncogene 1997 14: 1607-1610).*
Chemokine CXCL10 (MeSH-NCBI, 1987).*
Lee et al. (99th AACR Annual Meeting, Apr. 12-16, 2008, Abstract #953).*
Greenbaum et al. (Genome Biology, 2003, vol. 4, Issue 9, pp. 117.1-117.8).*
Boyd (The Basic Science of Oncology, 1992, McGraw-Hill, Inc., p. 379).*
Singh et al (Glycobiology, 2001, vol. 11, pp. 587-592).*
Matsushita et al. (FEBS Letters, 1999, vol. 443, pp. 348-352).*
Jiang et al (J. Biol. Chem. 2003, 278(7) 4763-4769).*
Yao et al. (Blood Sep. 1, 2000 96:1900-1905).*
Lind et al. (Cellular OncologyDec. 15, 2006 28:259-272).*
Ma et al. "Low Expression of XIAP-Associated Factor 1 in Human Colorectal Cancers." *Chinese J. Digest. Dis.* 6.1(2005):10-14.
Shuiping et al. "Restoration of XAF1 Expression Inhibits Gastric and Colonic Tumorigenesis in vivo." *Digest. Dis. Week Abs. Itinerary Planner.* 2003(2003). (Abstract #M1026).
Zou et al. "Correlation Between the Single-Site CpG Methylation and Expression Silencing of the XAF1 Gene in Human Gastric and Colon Cancers." *Gastroenterol.* 131.6(2006):1835-1843.
Abe et al. (1981), Proceedings of the National Academy of Sciences (USA), 78:4990-4994.
Ahuja et al. (2001), Molecular Pharmacology, 59:765-773.
Bischoff et al. (1999), Journal of the National Cancer Institute, 91:2118-2123.
Cowen et al. (1994), Critical Care Clinics, 10:53-72.
Crowe et al. (2004), Breast Cancer Research, 6:R546-R555.
Ebert et al. (1976), Cancer Research, 36:1809-1813.
Escarce et al. (1990), JAMA, 264:2389-2394.
Friend et al. (1971), Proceedings of the National Academy of Sciences (USA), 68:378-382.
Garattini et al. (2004), Current Pharmaceutical Design, 10:433-448.
Garattini et al. (2004), Journal of Chemotherapy, 16:70-73.
Gorgun et al. (2002), Blood, 100:1399-1403.
Hayashi et al. (1979), Gann, 70:235-238.
Huberman et al. (1979), Proceedings of the National Academy of Sciences (USA), 76:1293-1297.
Klipper-Aurbach et al. (1995), Medical Hypotheses, 45:486-490.
Knaus, et al. (1991), Chest, 100:1619-1636.
Levin (1996), American Journal of Public Health, 86:628-629.
Lind et al. (2006), Cellular Oncology, 28:259-272.
Lotem et al. (1975), Int. J. Cancer; 15:731-740.
Lotem et al. (1979), Proceedings of the National Academy of Sciences (USA), 76:5158-5162.

(Continued)

*Primary Examiner* — Peter J Reddig
(74) *Attorney, Agent, or Firm* — Mintz Levin Cohn Ferris Glovsky and Popeo, P.C.; Ivor R. Elrifi; Brian P. Hopkins, Esq.

(57) ABSTRACT

The present invention relates to methods and kits for the detection of predetermined biomarkers for early diagnosis and management of cancer, and in particular, colorectal cancer.

3 Claims, 19 Drawing Sheets

(56) References Cited

OTHER PUBLICATIONS

Marks et al. (1987), Cancer Research, 47:659-666.
Martinez et al. (1998), American Journal of Epidemiology, 148:17-19.
Metcalf (1985), Science, 229:16-22.
Morin et al. (1984), Cancer Research, 44:2807-2812.
O'Marcaigh et al. (1993), Clinical Pediatrics, 32:485-491.
Reuben et al. (1976), Proceedings of the National Academy of Sciences(USA), 73:862-866.
Rigas et al. (2005), The Oncologist, 10:22-33.
Sachs (1978), Nature, 274:535-539.
Scher et al. (1982), Biochemical and Biophysical Research Communications, 109:348-354.
Scher et al. (1983), Experimental Hematology, 11:490-498.
Schultz (1996), Teitz, Fundamentals of Clinical Chemistry, $4^{th}$ Edition, Chapter 14, pp. 192-199.
Schwartz et al. (1982), Cancer Research, 42:2651-2655.
Schwartz et al. (1983), Cancer Research, 43: 2725-2730.
Schwartz et al. (1983), Proceedings of the American Association for Cancer Research, 24:18, Abstract 71.
Simeone et al. (2004), Cellular and Molecular Life Sciences, 61:1475-1484.
Slattery et al. (1998), American Journal of Epidemiology, 148:4-16.
Sugano et al. (1973), Bibl. Hematol., 39:943-954.
Sun et al. (1999), Clinical Cancer Research, 5:431-437.
Takenaga et al. (1980), Cancer Research, 40:914-919.
Tanaka et al. (1975), Proceedings of the National Academy of Sciences (USA), 72:1003-1006.
Terada et al. (1978), Proceedings of the National Academy of Sciences (USA), 75:2795-2799.
Therianos et al. (2004), American Journal of Pathology, 164:795-806.
Velculescu et al. (1995), Science, 270:484-487.
Wilcoxon (1945), Biometrics Bulletin, 1:80-83.
Wirth et al. (2002), Proteomics, 2:1445-1451.
Zweig, et al. (1992), Clinical Chemistry, 38:1425-1428.

\* cited by examiner

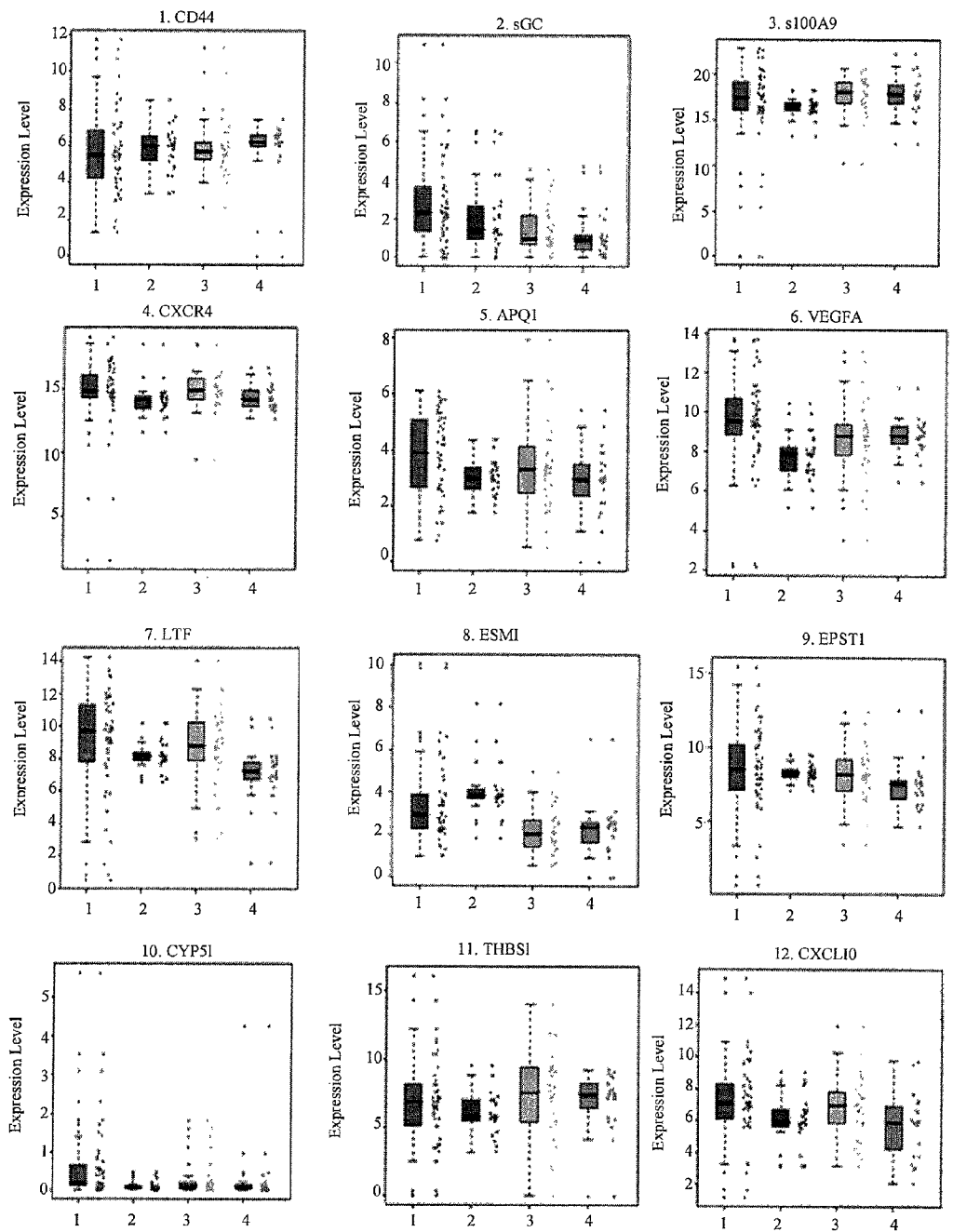

SEQUENCE LISTING

<160> NUMBER OF SEQ ID NOS: 104

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agctgtggag aagggaaatg                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
ttctttggga ctgggttgtc                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcccttccag caataagtgg                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttgaagcaca gcaagctcag                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aactggagct gatggacaca                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctcccccatt gacatccata                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccacaaatgg catctacacg                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 8
cccagccaat attctcctga                                                  20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aatgacctgg ctgatggtgt                                                  20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaggaccgag cagggttaat                                                  20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cctgccgatc ctaaatcaac                                                  20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tttcacaaga ccaccacagc                                                  20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cagcccaaag tgtgtgagaa                                                  20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
```
cggtcaaact gcccatactt                                                    20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gacttgctca gccagattca                                                    20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atggaatccc tgacccatct                                                    20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aagcacaatc caggcaactc                                                    20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggtgttgtcc ttccttgcat                                                    20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tattaccgtc caggggtgaa                                                    20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
attggcctgg caggtataga                                                    20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acctggagat gcagatcgaa                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctcggccatg acctcatatt                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
acgccagaac aacgaatacc                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ttcagatgac acgaccttgc                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tcatgcgttc tcctcagatg                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aatccactgg tgaaccaagc                                              20

<210> SEQ ID NO 27

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ccacgtgttg agatcattgc                                               20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gattttgctc ccctctggtt                                               20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccttccaaga agagcagcaa                                               20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
atgcaaagac agcgtcctct                                               20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgacttgtgg gtggttgtgt                                               20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gagtcgatgc tgatcccaat                                               20

<210> SEQ ID NO 33
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 33
atgccttcct gctgaagatg                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cacgtaccca cttttggaca                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
agaatggcca gaactcctca                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
agctccaaat ggcacatagg                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
acgctggatg tttgagtgtg                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tgtagaaggg aaacgctgct                                              20

<210> SEQ ID NO 39
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 39
ccttggatgg gtattccaga                                               20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tccatgagag cctttctcc                                                20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tggacaggga ggattttgag                                               20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
acctgaggct ttggattcct                                               20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ctggccgtaa actgctttgt                                               20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
agcccatcat tgttctggag                                               20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 45
agagccaaaa tccaccagac                                                      20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tgaggctttt cgaggtcagt                                                      20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
catggatggc atgaagtgtg                                                      20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ggaagaaggg gaatttcagg                                                      20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
atcctagcca tcctgtttgg                                                      20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tgaaattggg aggactcagg                                                      20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51

```
gcaatgggac ctttgagtgt                                              20
```

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52

```
tcttgccaaa gtcactgctg                                              20
```

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53

```
ctgcgtcatg atgttcacct                                              20
```

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54

```
gatcgctcgc tctgaaactt                                              20
```

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55

```
acgctgggca acattaagag                                              20
```

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56

```
gagatttgga gaagcggatg                                              20
```

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57

```
atttccctga caccatccag                                              20
```

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ctttgatcca cagggatg                                                   19

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ctggagacgt tgcatttgtg                                                 20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ttcaggcgtt ccaccttatc                                                 20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gcggagacca tcaagaatgt                                                 20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cagcgtgatt ttgagagtgg                                                 20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gagtgccaga tgttgcagaa                                                 20

```
<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gccaatcatg atgtcagcag                                              20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ttccaaggcc aatcctactc                                              20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
caggaaagtg aaggggaaga                                              20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
atgggaagta ctggcgattc                                              20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
cgcccagaga agaagaaaag                                              20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
caagtgtaat gggcatgctg                                              20

<210> SEQ ID NO 70
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
atcctactgg atggcaggaa                                                    20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
atttccatgc cgtctacagg                                                    20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
acgcccatct ttatcaccag                                                    20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cagctggaac gcaacataga                                                    20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
tttgtgtcca ggtcctccat                                                    20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
aaggcagctg ctcacgtatt                                                    20

<210> SEQ ID NO 76
<211> LENGTH: 20
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 76
atagcgatgt gggaatcacc                                               20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tgtcacagcc tgtttctgga                                               20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gttcttggct ttcaggatgg                                               20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cctcaatgaa cgggacaact                                               20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gttctggtgg ccatcttcat                                               20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tgcccagata ttggtgtcct                                               20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued

```
primer

<400> SEQUENCE: 82
ggcatgtttt ctcagcaggt                                                 20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
aagcccctga actgtgatga                                                 20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gccagtgaaa gggaaacaga                                                 20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
taaccaggct ggaagaagca                                                 20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tgtctcctgt ctccgctttt                                                 20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gaacccaaac aaaggcagag                                                 20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 88
cctggctcaa gcatgtcata                                               20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
caggacattg ctgtgctttg                                               20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ggctgcttct tccaacaatg                                               20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
agtccaacat caccatgcag                                               20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
gcgagtctgt gttttttgcag                                              20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
gggcagaatc atcacgaagt                                               20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
```

-continued tggtgatgtt ggactcctca                                          20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
tcacgtcatc cagcagagaa                                          20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
cggcaggcat actcatcttt                                          20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
atcccatcac catcttccag                                          20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
gttcacaccc atgacgaaca                                          20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
tgctcgagat gtgatgaagg                                          20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
tcccctgttg actggtcatt                                          20

```
<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tcgacaatgg cagcatctac                                                  20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
cttttcagca agtgggaagg                                                  20

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 103
tttttttttt tttttttttv n                                                21

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
actgaacctg accgtaca                                                    18
```

BIOMARKER COMBINATIONS FOR COLORECTAL CANCER

The present application is a National Phase of International Application No. PCT/IB2008/003175, filed on Jun. 4, 2008, and claiming priority from U.S. Provisional Patent Application Ser. No. 60/933,272, titled "Biomarker Combinations For Colorectal Cancer and Methods of Use Thereof", filed Jun. 4, 2007, each of which is incorporated by reference herein in its entirety for all purposes.

FIELD OF THE INVENTION

The present invention relates generally to a profile of peripheral blood surrogate biomarkers related to solid tumors and methods of use thereof, for screening, prevention, diagnosis, therapy, monitoring, and prognosis of colorectal cancer.

BACKGROUND OF THE INVENTION

Screening and monitoring assays are essential for the early detection and management of cancer. Cancer screening and monitoring tests, such as blood tests collected in a medical environment, can be used for large-scale screening of clinically healthy (or "asymptomatic") individuals, for diagnosis, for prediction tests or for disease monitoring in subjects.

The advantage of blood-based remote samples for such applications is that it is very convenient for a subject to provide a sample, and therefore compliance is much higher in a test population. In the case of colorectal cancer, less than 20% of people at risk are screened, mainly due to psychological barriers induced by uncomfortable and invasive screening methodologies, such as colonoscopy.

Accordingly, there is a need in the art for approaches that afford early detection and treatment of solid tumors, such as colorectal cancer, that have the added benefit of being cost-effective, rapid, and minimally invasive, preferably noninvasive. Additional utility allows for prognosis of cancers, monitoring subject treatment of cancers, and detecting relapse of cancers, as well as the discovery of new therapeutic interventions for treating cancers, such as solid tumors.

SUMMARY OF THE INVENTION

The present invention is premised on the discovery that disease-associated biomarkers can be identified in serum or other bodily fluids long before overt disease is apparent. The presence or absence of these biomarkers from the serum footprints of patients suffering from colorectal cancer can be used as early diagnostic tools, for which treatment strategies can be devised and administered to prevent, delay, ameliorate, or reverse the formation of neoplastic colorectal cells. One or several of the disease-associated biomarkers of the present invention can be used to diagnose subjects suffering from colorectal cancer, or advantageously, to diagnose those subjects who are asymptomatic for colorectal cancer.

The present invention thus concerns biomarker profiles and methods for analyzing multiple peripheral blood surrogate biomarkers implicated in solid tumors, particularly solid tumors implicated in colorectal cancer. These biomarkers are useful for genetic testing for solid tumors, including genetic predisposition to solid tumors, early detection of solid tumors, diagnosis of solid tumors, testing for cancerous tissue typing, and other methods of use thereof.

The disclosed methods, kits, and biomarker profiles of the present invention are designed to screen colorectal cancer preferably with a sensitivity equal or superior to 70% and specificity equal or superior to 95%. The disclosed methods are also capable of quantifying the relative and absolute amounts of targeted genes and/or gene products related to solid tumors.

In general, the methods and biomarker profiles of the present invention are useful for obtaining quantitative information about the expression of many different genes related to solid tumors in a sample that can comprise peripheral blood and which can contain as little as a single cell.

In one embodiment, the cancer comprises colorectal cancer. The level of biomarkers can be measured electrophoretically or immunochemically, wherein the immunochemical detection can be achieved by radioimmunoassay, immunofluorescence assay or by an enzyme-linked immunosorbent assay. Preferably, the level of biomarkers is measured by real-time PCR.

The sample from the subject can comprise, for example, whole blood, serum, plasma, blood cells, endothelial cells, tissue biopsies, lymphatic fluid, ascites fluid, interstitital fluid, bone marrow, cerebrospinal fluid (CSF), saliva, mucous, sputum, sweat, or urine.

Accordingly, the present invention provides a method of diagnosing or identifying colorectal cancer in a subject, comprising: measuring an effective amount of one or more CLR-MARKERS or a metabolite thereof in a sample from the subject; and comparing the amount to a reference value, wherein an increase or decrease in the amount of the one or more CLRMARKERS relative to the reference value indicates that the subject suffers from colorectal cancer. The reference value can comprise an index value, a value derived from one or more colorectal cancer risk prediction algorithms or computed indices, a value derived from a subject not suffering from colorectal cancer, or a value derived from a subject diagnosed with or identified as suffering from colorectal cancer. In some embodiments, the subject comprises one who has been previously diagnosed as having colorectal cancer, one who has not been previously diagnosed as having colorectal cancer, or one who is asymptomatic for the colorectal cancer.

The present invention also provides a method for monitoring the progression of colorectal cancer in a subject, comprising measuring an effective amount of one or more CLR-MARKERS in a first sample from the subject at a first period of time; measuring an effective amount of one or more CLR-MARKERS in a second sample from the subject at a second period of time; and comparing the amounts of the one or more CLRMARKERS detected in step (a) to the amount detected in step (b), or to a reference value. In one embodiment, the monitoring comprises evaluating changes in the risk of developing colorectal cancer. The subject can comprise one who has previously been treated for colorectal cancer, one who has not been previously treated for the colorectal cancer, or one who has not been previously diagnosed with or identified as suffering from colorectal cancer. In certain embodiments, the first sample is taken from the subject prior to being treated for colorectal cancer and the second sample is taken from the subject after being treated for colorectal cancer. In other embodiments, the monitoring further comprises selecting a treatment regimen for the subject and/or monitoring the effectiveness of a treatment regimen for colorectal cancer, which can comprise surgical intervention, colorectal cancer-modulating agents, or combinations thereof. In some embodiments, the reference value comprises an index value, a value derived from one or more colorectal cancer risk prediction algorithms or computed indices, a value derived from a subject not suffering from colorectal cancer, or a value derived from a subject diagnosed with or identified as suffering from colorectal cancer.

In another aspect, the present invention provides a method of treating a subject diagnosed with or identified as suffering from colorectal cancer comprising: measuring an effective amount of one or more CLRMARKERS or metabolites thereof present in a first sample from the subject at a first period of time; and treating the subject with one or more colorectal cancer-modulating agents until the amounts of the one or more CLRMARKERS or metabolites thereof return to a reference value measured in one or more subjects at low risk for developing colorectal cancer, or a reference value measured in one or more subjects who show improvements in colorectal cancer risk factors as a result of treatment with the one or more colorectal cancer-modulating agents.

The one or more colorectal-modulating agents can comprise an alkylating agent, an antibiotic agent, an antimetabolic agent, a hormonal agent, a plant-derived agent, a retinoid agent, a tyrosine kinase inhibitor, a biologic agent, a gene therapy agent, a histone deacetylase inhibitor, other anticancer agent, or combinations thereof. The improvements in colorectal cancer risk factors as a result of treatment with one or more colorectal cancer-modulating agents can comprise a reduction in polyp formation, a reduction in polyp size, a reduction in polyp number, a reduction in symptoms of ulcerative colitis, inflammatory bowel disease, and/or Crohn's disease, or combinations thereof.

The present invention also provides a kit comprising CLRMARKER detection reagents that detect one or more CLRMARKERS, a sample derived from a subject having normal control levels, and optionally instructions for using the reagents in the methods of the invention. In one embodiment, the detection reagents further comprise one or more antibodies or fragments thereof, one or more aptamers, one or more oligonucleotides, or combinations thereof.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from the following detailed description and claims.

BRIEF DESCRIPTION OF THE DRAWINGS

The following Detailed Description, given by way of example, but not intended to limit the invention to specific embodiments described, may be understood in conjunction with the accompanying figure, incorporated herein by reference, in which:

FIGS. 1A-1E provide a plurality of graphs depicting the distribution of genes according to the classes of samples corresponding to controls (CON), inflammatory bowel diseases (IBD), advanced polyps/adenomas (POL), and carcinomas (CAR).

DETAILED DESCRIPTION OF THE INVENTION

Figure 1B:
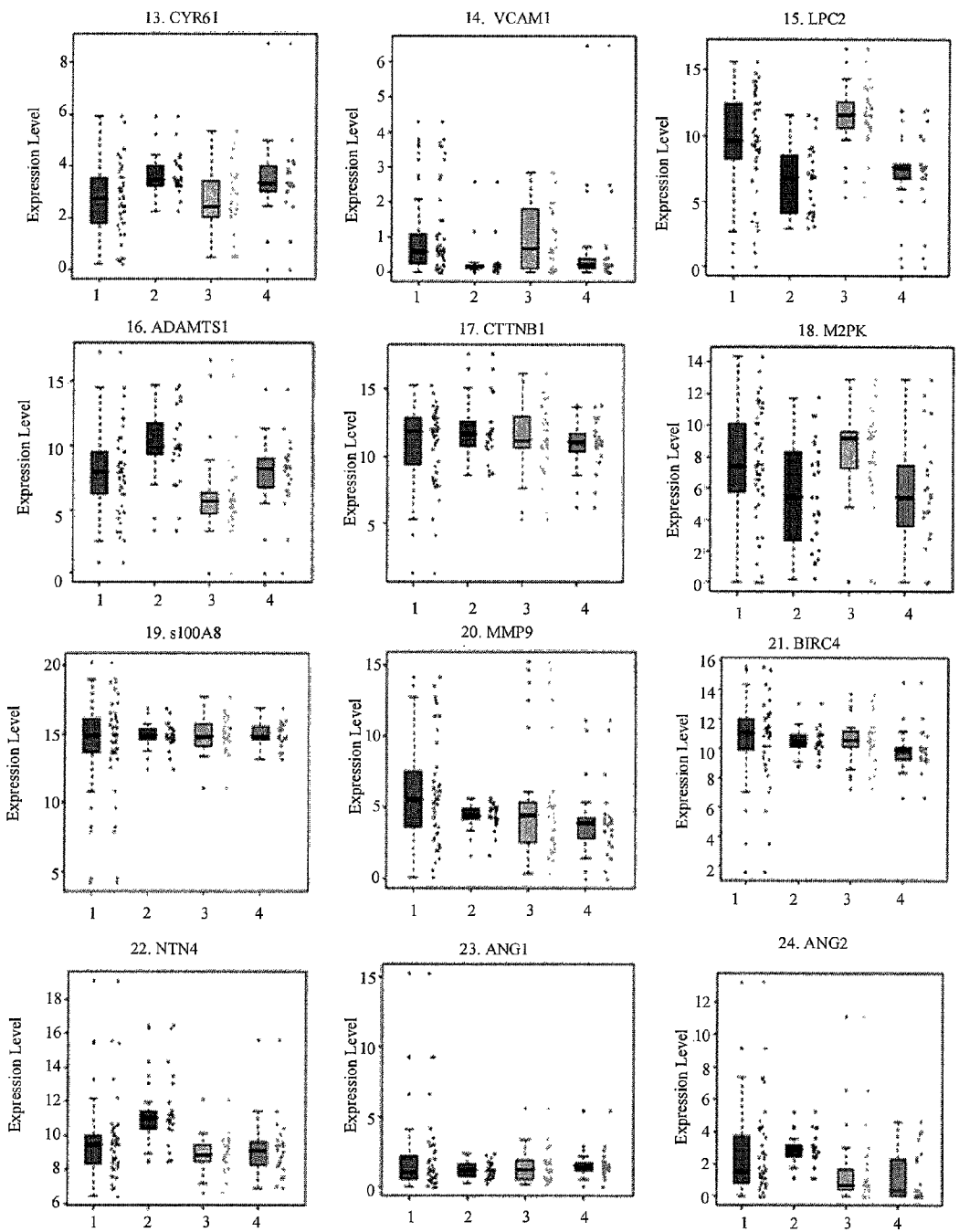
Figure 1C:
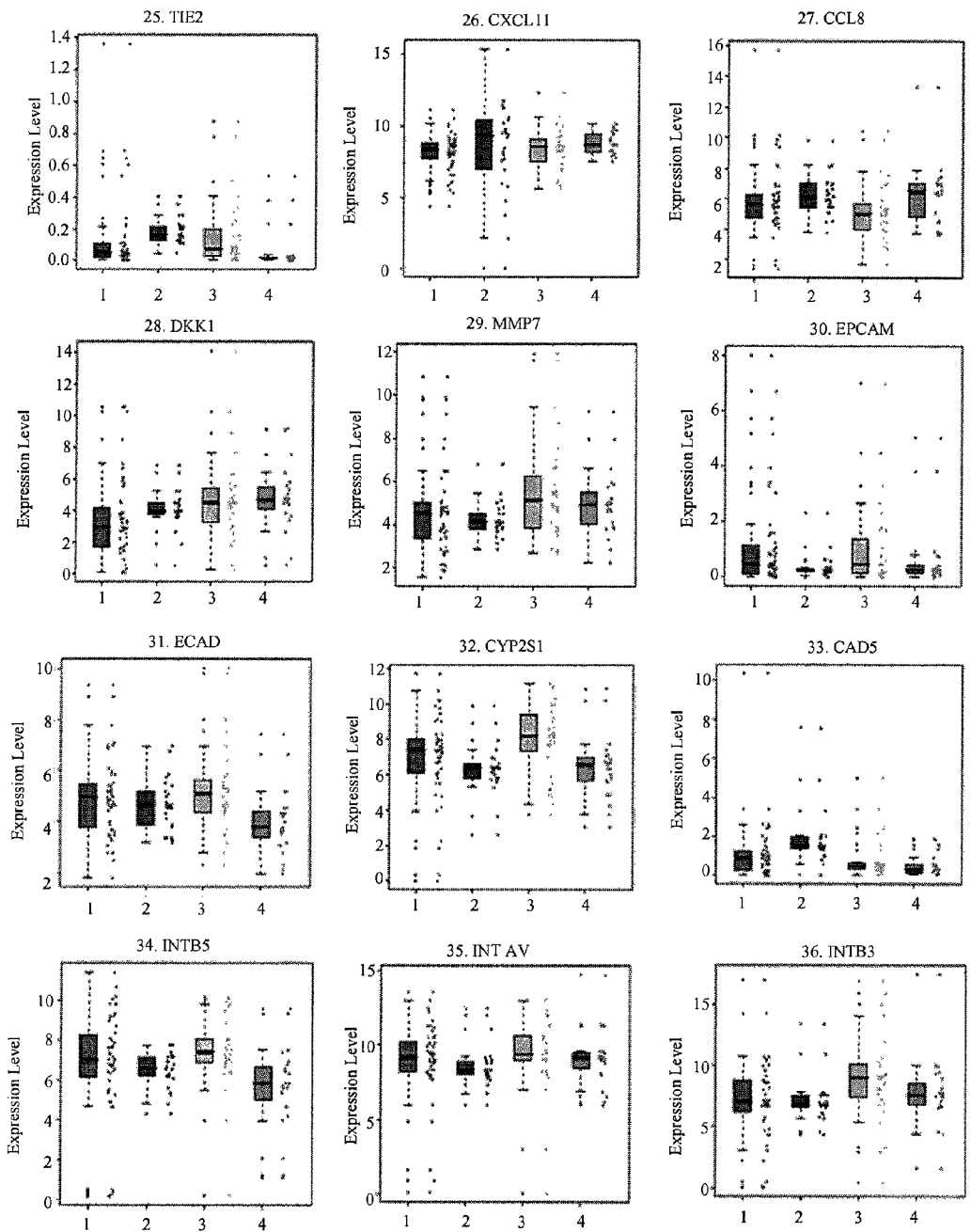
Figure 1D:
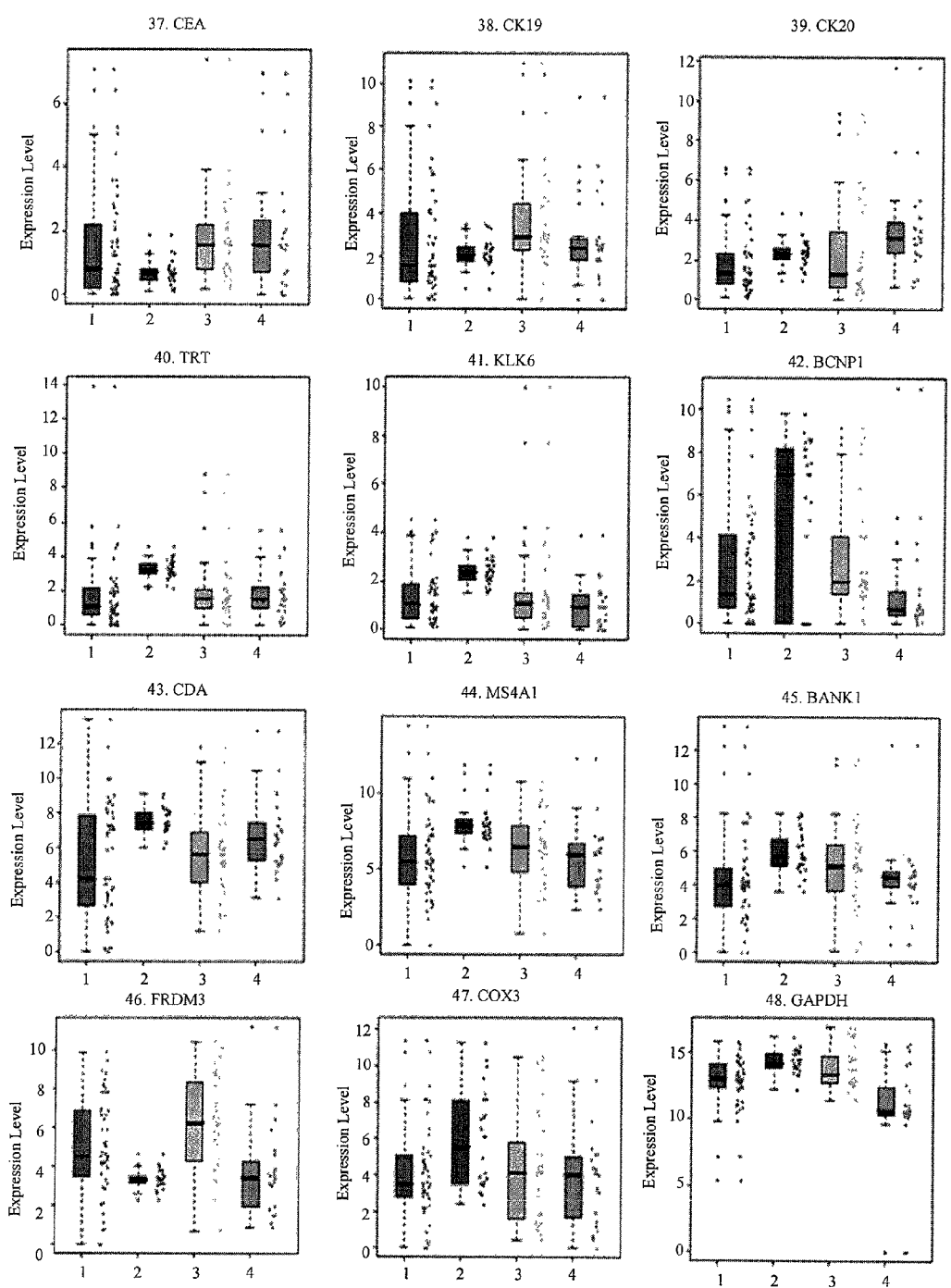
Figure 1E:
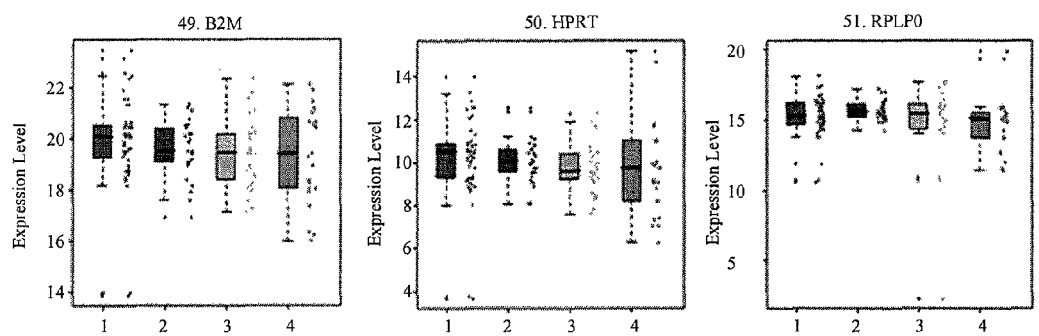

Accordingly, the present invention provides biomarkers of solid tumors that, when used together in combinations of one or more and preferably two or more, such biomarker combinations can be used to detect colorectal cancer.

As used herein, "a," an" and "the" include singular and plural referents unless the context clearly dictates otherwise. Thus, for example, reference to "an active agent" or "a pharmacologically active agent" includes a single active agent as well as two or more different active agents in combination, reference to "a carrier" includes mixtures of two or more carriers as well as a single carrier, and the like.

A "biomarker" in the context of the present invention is a molecular indicator of a specific biological property; a biochemical feature or facet that can be used to detect colorectal cancer. "Biomarker" encompasses, without limitation, proteins, nucleic acids, and metabolites, together with their polymorphisms, mutations, variants, modifications, subunits, fragments, protein-ligand complexes, and degradation products, protein-ligand complexes, elements, related metabolites, electrolytes, elements, and other analytes or sample-derived measures. Biomarkers can also include mutated proteins or mutated nucleic acids. Biomarkers can also refer to non-analyte physiological markers of health status encompassing other clinical characteristics or risk factors of colorectal cancer such as, without limitation, age, ethnicity, and family history of cancer. An "analyte" as used herein can mean any substance to be measured.

"Colon cancer" refers to cancers and/or neoplasms that form in the tissues of the colon (the longest part of the large intestine). Most colon cancers are adenocarcinomas (cancers that begin in cells that make and release mucus and other fluids). "Rectal cancer" refers to cancers and/or neoplasms that forms in the tissues of the rectum (the last several inches of the large intestine before the anus). "Colorectal cancer" in the context of the present invention refers to cancers that arise in either the colon or the rectum.

"Measuring" or "measurement" means assessing the presence, absence, quantity or amount (which can be an "effective amount") of either a given substance within a clinical or subject-derived sample, including qualitative or quantitative concentration levels of such substances, or otherwise evaluating the values or categorization of a subject's clinical parameters.

A "sample" in the context of the present invention is a biological sample isolated from a subject and can include, by way of example and not limitation, whole blood, serum, plasma, blood cells, endothelial cells, tissue biopsies, lymphatic fluid, ascites fluid, interstitital fluid (also known as "extracellular fluid" and encompasses the fluid found in spaces between cells), bone marrow, cerebrospinal fluid (CSF), saliva, mucous, sputum, sweat, urine, or any other secretion, excretion, or other bodily fluids.

A "subject" in the context of the present invention is preferably a mammal. The mammal can be a human, non-human primate, mouse, rat, dog, cat, horse, or cow, but are not limited to these examples. Mammals other than humans can be advantageously used as subjects that represent animal models of colorectal cancer. A subject can be male or female. A subject can be one who has been previously diagnosed with or identified as suffering from or having colorectal cancer, and optionally, but need not have already undergone treatment for the colorectal cancer. A subject can also be one who is not suffering from colorectal cancer. A subject can also be one who has been diagnosed with or identified as suffering from colorectal cancer, but who show improvements in the disease (such as, for example, a decrease in tumor size) as a result of receiving one or more treatments for colorectal cancer. Alternatively, a subject can also be one who has not been previously diagnosed or identified as having colorectal cancer. For example, a subject can be one who exhibits one or more risk factors for colorectal cancer, or a subject who does not exhibit risk factors for colorectal cancer, or a subject who is asymptomatic for colorectal cancer. A subject can also be one who is suffering from or at risk of developing colorectal cancer.

Proteins, peptides, nucleic acids, polymorphisms, and metabolites whose levels are changed, altered, or modified in subjects who have colorectal cancer, or are predisposed to developing colorectal cancer are summarized in Table 1 and are collectively referred to herein as, inter alia, "colorectal cancer-associated proteins", "CLRMARKER polypeptides", or "CLRMARKER proteins". The corresponding nucleic acids encoding the polypeptides are referred to as "colorectal cancer-associated nucleic acids", "colorectal cancer-associated genes", "CLRMARKER nucleic acids", or "CLR-MARKER genes". Unless indicated otherwise, "CLRMARKER", "colorectal cancer-associated proteins", "colorectal cancer-associated nucleic acids" are meant to refer to any of the sequences disclosed herein. The corresponding metabolites of the CLRMARKER proteins or nucleic acids can also be measured, herein referred to as "CLRMARKER metabolites". A CLRMARKER "metabolite" in the context of the present invention can comprise a portion of a full length polypeptide. No particular length is implied by the term "portion." A CLRMARKER metabolite can be less than 500 amino acids in length, e.g., less than or equal to 400, 350, 300, 250, 200, 150, 100, 75, 50, 35, 26, 25, 15, or 10 amino acids in length. Calculated indices created from mathematically combining measurements of one or more, preferably two or more of the aforementioned classes of CLRMARKERS are referred to as "CLRMARKER indices". Proteins, nucleic acids, polymorphisms, mutated proteins and mutated nucleic acids, metabolites, and other analytes are, as well as common physiological measurements and indices constructed from any of the preceding entities, are included in the broad category of "CLRMARKERS".

Fifty-one (51) biomarkers have been identified as having altered or modified presence or concentration levels in subjects who have colorectal cancer, or who exhibit symptoms characteristic of colorectal cancer, such as the presence of polyps or growths inside the colon and rectum. Risk factors for colorectal cancer include, without limitation, the presence of polyps or growths inside the colon and rectum that may become cancerous, a diet that is high in fat, family history or personal history of colorectal cancer, and ulcerative colitis, inflammatory bowel disease, or Crohn's disease. A reduction in risk factors as a result of, inter alia, surgical interventions like resection and colorectal cancer-modulating agents such as anti-cancer chemotherapy can comprise, for example, a reduction in polyp formation, a reduction in polyp size, a reduction in polyp number, and reductions or alleviation of symptoms of ulcerative colitis, inflammatory bowel disease, and/or Crohn's disease, or combinations thereof.

The performance and thus absolute and relative clinical usefulness of the invention may be assessed in multiple ways. Amongst the various assessments of performance, the invention is intended to provide accuracy in clinical diagnosis of cancer, and in particular, colorectal cancer.

Biomarkers

The biomarkers and methods of the present invention allow one of skill in the art to identify, diagnose, or otherwise assess those subjects who do not exhibit any symptoms of cancer or solid tumors, but who nonetheless may be at risk for developing cancer or solid tumors, or experiencing symptoms characteristic of a cancerous condition.

Table 1 provides information including a non-exhaustive list of candidate peripheral blood surrogate biomarkers for solid tumors according to the invention. One skilled in the art will recognize that the biomarkers presented herein encompasses all forms and variants, including but not limited to, polymorphisms, isoforms, mutants, derivatives, precursors including nucleic acids and pro-proteins, cleavage products, receptors (including soluble and transmembrane receptors), ligands, protein-ligand complexes, and post-translationally modified variants (such as cross-linking or glycosylation), fragments, and degradation products, as well as any multi-unit nucleic acid, protein, and glycoprotein structures comprised of any of the biomarkers as constituent subunits of the fully assembled structure. All biomarkers expression within blood samples have been validated through experimentation.

TABLE 1

CLRMARKERS

| # | Biomarkers & References | Abbrev. | Acces. Nb | Forward Primer | Reverse Primer | Amplicon |
|---|---|---|---|---|---|---|
| 1 | ADAM metallopeptidase with thrombospondin type 1 | ADAMTS1 | NM_006988 | agctgtggagaagggaaatg | ttctttgggactgggttgtc | 182 |
| 2 | angiopoietin 1 | ANG1 | NM_001146 | tcccttccagcaataagtgg | ttgaagcacagcaagctcag | 185 |
| 3 | angiopoietin 1 | ANG1(2) | NM_001146 | aactggagctgatggacaca | ctcccccattgacatccata | 216 |
| 4 | angiopoietin 2 | ANG2 | NM_001147 | ccacaaatggcatctacacg | cccagccaatattctcctga | 190 |
| 5 | aquaporin 1 | AQP1 | NM_198098 | aatgacctggctgatggtgt | aaggaccgagcagggttaat | 212 |
| 6 | XIAP associated factor-1 (XAF1 ou BIRC4BP) | BIRC4BP | NM_199139 | cctgccgatcctaaatcaac | tttcacaagaccaccacagc | 170 |
| 7 | cadherin 5 | CAD5 | NM_001795 | CAGCCCAAAGTGTGTGAGAA | CGGTCAAACTGCCCATACTT | 185 |
| 8 | chemokine (C-C motif) ligand 8 | CCL8 | NM_005623 | gacttgctcagccagattca | atggaatccctgacccatct | 199 |
| 9 | CD44 molecule | CD44 | NM_000610 | aagcacaatccaggcaactc | ggtgttgtccttccttgcat | 183 |
| 10 | carcinoembryonic-antigen | CEA | M29540 | tattaccgtccaggggtgaa | attggcctggcaggtataga | 165 |
| 11 | cytokeratin 19 | CK19 | NM_002276 | acctggagatgcagatcgaa | ctcggccatgacctcatatt | 188 |
| 12 | cytokeratin 20 | CK20 | NM_019010 | acgccagaacaacgaatacc | ttcagatgacacgaccttgc | 208 |
| 13 | catenin (cadherin-associated protein), beta 1 | CTNNB1 | NM_001904 | tcatgcgttctcctcagatg | aatccactggtgaaccaagc | 186 |
| 14 | chemokine (C-X-C motif) ligand 10 | CXCL10 | NM_001565 | ccacgtgttgagatcattgc | gattttgctcccctctggtt | 146 |
| 15 | chemokine (C-X-C motif) ligand 11 | CXCL11 | NM_005409 | ccttccaagaagagcagcaa | atgcaaagacagcgtcctct | 165 |
| 16 | chemokine (C-X-C motif) receptor 4 | CXCR4 | NM_003467 | tgacttgtgggtggttgtgt | gagtcgatgctgatcccaat | 213 |
| 17 | cytochrome P450, family 2, subfamily S, polypeptide 1 | CYP2S1 | NM_030622 | atgccttcctgctgaagatg | cacgtacccactttggaca | 180 |
| 18 | lanosterol 14-alpha demethylase cytochrome P450 | CYP51 | U23942 | agaatggccagaactcctca | agctccaaatggcacatagg | 189 |
| 19 | cysteine-rich, angiogenic inducer, 61 | CYR61 | NM_001554 | acgctggatgtttgagtgtg | tgtagaagggaaacgctgct | 213 |
| 20 | dickkopf homolog 1 (*Xenopus laevis*) | DKK1 | NM_012242 | ccttggatgggtattccaga | tcatgagagccttttctcc | 200 |
| 21 | e-cadherin (epithelial) | ECAD | NM_004360 | tggacagggaggattttgag | acctgaggctttggattcct | 190 |
| 22 | tumor-associated calcium signal transducer 1 | EP-CAM | NM_002354 | ctggccgtaaactgctttgt | agcccatcattgttctggag | 182 |
| 23 | epithelial stromal interaction 1 (breast) | EPSTI1 | NM_033255 | agagccaaaatccaccagac | tgaggcttttcgaggtcagt | 192 |
| 24 | endothelial cell-specific molecule 1 | ESM1 | NM_007036 | catggatggcatgaagtgtg | ggaagaagggaatttcagg | 194 |

TABLE 1-continued

CLRMARKERS

| # | Biomarkers & References | Abbrev. | Acces. Nb | Forward Primer | Reverse Primer | Amplicon |
|---|---|---|---|---|---|---|
| 25 | integrin alpha V | INTAV | MN_002205 | atcctagccatcctgtttgg | tgaaattgggaggactcagg | 159 |
| 26 | integrin beta 3 | INTB3 | NM_000212 | GCAATGGGACCTTTGAGTGT | TCTTGCCAAAGTCACTGCTG | 195 |
| 27 | integrin beta 5 | INTB5 | NM_002213 | CTGCGTCATGATGTTCACCT | GATCGCTCGCTCTGAAACTT | 219 |
| 28 | lipocalin 2 (oncogene 24p3) | LPC2 | NM_005564 | acgctgggcaacattaagag | gagatttggagaagcggatg | 199 |
| 29 | kallikrein-related peptidase 6 (zyme or neurosin or protM) | KLK6 | NM_002774 | atttccctgacaccatccag | ctttgatccacaggggatg | 215 |
| 30 | lactoferrin | LTF | NM_002343 | ctggagacgttgcatttgtg | ttcaggcgttccaccttatc | 214 |
| 31 | M2-Pyruvate kinase | M2-PK | NM_002654 | gcggagaccatcaagaatgt | cagcgtgattttgagagtgg | 180 |
| 32 | matrix metallopeptidase 7 | MMP7 | NM_002423 | gagtgccagatgttgcagaa | gccaatcatgatgtcagcag | 209 |
| 33 | matrix metallopeptidase 9 | MMP9 | NM_004994 | ttccaaggccaatcctactc | caggaaagtgaaggggaaga | 183 |
| 34 | matrix metallopeptidase 9 | MMP9(2) | NM_004994 | atgggaagtactggcgattc | cgcccagagaagaagaaaag | 148 |
| 35 | netrin 4 | NTN4 | NM_021229 | caagtgtaatgggcatgctg | atcctactggatggcaggaa | 209 |
| 36 | S100 calcium binding protein A8 | S100A8 | NM_002964 | atttccatgccgtctacagg | acgcccatctttatcaccag | 166 |
| 37 | S100 calcium binding protein A9 | S100A9 | NM_002965 | cagctggaacgcaacataga | tttgtgtccaggtcctccat | 188 |
| 38 | guanylyl cyclase c - soluble guanylyl cyclase | sGC | Y15723 | aaggcagctgctcacgtatt | atagcgatgtgggaatcacc | 187 |
| 39 | telomerase reverse transcriptase | TERT | NM_198253 | tgtcacagcctgtttctgga | gttcttggctttcaggatgg | 210 |
| 40 | thrombospondin 1 | THBS1 | NM_003246 | cctcaatgaacgggacaact | gttctggtggccatcttcat | 190 |
| 41 | TEK tyrosine kinase, endothelial | TIE2 | NM_000459 | tgcccagatattggtgtcct | ggcatgttttctcagcaggt | 197 |
| 42 | TEK tyrosine kinase, endothelial | TIE2(2) | NM_000459 | aagccccctgaactgtgatga | gccagtgaaagggaaacaga | 241 |
| 43 | vascular cell adhesion molecule 1 | VCAM1 | NM_080682 | taaccaggctggaagaagca | tgtctcctgtctccgctttt | 185 |
| 44 | vascular cell adhesion molecule 1 | VCAM1(1) | NM_080682 | gaacccaaacaaaggcagag | cctggctcaagcatgtcata | 130 |
| 45 | vascular endothelial growth factor A | VEGFA | NM_001033756 | caggacattgctgtgctttg | ggctgcttcttccaacaatg | 188 |
| 46 | vascular endothelial growth factor A | VEGFA(1) | NM_001033756 | agtccaacatcaccatgcag | gcgagtctgtgtttttgcag | 216 |
| 47 | vascular endothelial growth factor A | VEGFA(2) | NM_001025366 | gggcagaatcatcacgaagt | tggtgatgttggactcctca | 211 |
| | Reference genes | | | | | |
| 48 | beta-2-microglobulin | B2M | NM_004048 | tcacgtcatccagcagagaa | cggcaggcatactcatcttt | 212 |
| 49 | glyceraldehyde-3-phosphate dehydrogenase | GAPDH | NM_002046 | atcccatcaccatcttccag | gttcacacccatgacgaaca | 194 |
| 50 | hypoxanthine phosphoribosyltransferase | HPRT | L29382 | tgctcgagatgtgatgaagg | tcccctgttgactggtcatt | 192 |

TABLE 1-continued

CLRMARKERS

| # | Biomarkers & References | Abbrev. | Acces. Nb | Forward Primer | Reverse Primer | Amplicon |
|---|---|---|---|---|---|---|
| 51 | ribosomal protein, large, P0 | RPLP0 | NM_001002 | tcgacaatggcagcatctac | cttttcagcaagtgggaagg | 215 |

TABLE 2

Sequence identifiers

| Biomarker (from Table 1) | Forward primer (SEQ ID NO) | Reverse Primer (SEQ ID NO) |
|---|---|---|
| ADAMTS1 | 1 | 2 |
| ANG1 | 3 | 4 |
| ANG1(2) | 5 | 6 |
| ANG2 | 7 | 8 |
| AQP1 | 9 | 10 |
| BIRC4BP | 11 | 12 |
| CAD5 | 13 | 14 |
| CCL8 | 15 | 16 |
| CD44 | 17 | 18 |
| CEA | 19 | 20 |
| CK19 | 21 | 22 |
| CK20 | 23 | 24 |
| CTNNB1 | 25 | 26 |
| CXCL10 | 27 | 28 |
| CXCL11 | 29 | 30 |
| CXCR4 | 31 | 32 |
| CYP2S1 | 33 | 34 |
| CYP51 | 35 | 36 |
| CYR61 | 37 | 38 |
| DKK1 | 39 | 40 |
| ECAD | 41 | 42 |
| EP-CAM | 43 | 44 |
| EPSTI1 | 45 | 46 |
| ESM1 | 47 | 48 |
| INTAV | 49 | 50 |
| INTB3 | 51 | 52 |
| INTB5 | 53 | 54 |
| LPC2 | 55 | 56 |
| KLK6 | 57 | 58 |
| LTF | 59 | 60 |
| M2-PK | 61 | 62 |
| MMP7 | 63 | 64 |
| MMP9 | 65 | 66 |
| MMP9(2) | 67 | 68 |
| NTN4 | 69 | 70 |
| S100A8 | 71 | 72 |
| S100A9 | 73 | 74 |
| sGC | 75 | 76 |
| TERT | 77 | 78 |
| THBS1 | 79 | 80 |
| TIE2 | 81 | 82 |
| TIE2(2) | 83 | 84 |
| VCAM1 | 85 | 86 |
| VCAM1(1) | 87 | 88 |
| VEGFA | 89 | 90 |
| VEGFA(1) | 91 | 92 |
| VEGFA(2) | 93 | 94 |
| B2M | 95 | 96 |
| GAPDH | 97 | 98 |
| HPRT | 99 | 100 |
| RPLP0 | 101 | 102 |

One or more, preferably two or more CLRMARKERS can be detected in the practice of the present invention. For example, one (1), two (2), three (3), five (5), ten (10), fifteen (15), twenty (20), twenty-five (25), thirty (30), thirty-five (35), forty (40), forty-five (45), fifty (50) or more CLRMARKERS can be detected. In some aspects, all 51 CLRMARKERS disclosed herein can be detected. Preferred ranges from which the number of CLRMARKERS can be detected include ranges bounded by any minimum selected from between one and 51, particularly two, three, four, five, six, seven, eight, nine, ten, twelve, fifteen, twenty, twenty-five, thirty, forty, fifty, paired with any maximum up to the total known CLRMARKERS, particularly one, two, five, ten, twenty, and twenty-five. Particularly preferred ranges include one to two (1-2), one to five (1-5), one to ten (1-10), one to fifteen (1-15), one to twenty (1-20), one to twenty-five (1-25), one to thirty (1-30), one to thirty-five (1-35), one to forty (1-40), one to forty-five (1-45), one to fifty (1-50), one to fifty-one (1-51), two to five (2-5), two to ten (2-10), two to fifteen (2-15), two to twenty (2-20), two to twenty-five (2-25), two to thirty (2-30), two to thirty-five (2-35), two to forty (2-40), two to forty-five (2-45), two to fifty (2-50), two to fifty-one (2-51), five to fifteen (5-15), five to twenty (5-20), five to twenty-five (5-25), five to thirty (5-30), five to thirty-five (5-35), five to forty (5-40), five to forty-five (5-45), five to fifty (5-50), five to fifty-one (5-51), ten to fifteen (10-15), ten to twenty (10-20), ten to twenty-five (10-25), and ten to thirty (10-30), ten to thirty-five (10-35), ten to forty (10-40), ten to forty-five (10-45), ten to fifty (10-50), ten to fifty-one (10-51), twenty to fifty (20-50), and twenty to fifty-one (20-51).

Detecting Biomarkers

The risk of developing colorectal cancer can be detected by examining an "effective amount" of CLRMARKER proteins, peptides, nucleic acids, polymorphisms, metabolites, and other analytes in a test sample (e.g., a subject derived sample) and comparing the effective amounts to reference or index values. An "effective amount" can be the total amount or levels of CLRMARKERS that are detected in a sample, or it can be a "normalized" amount, e.g., the difference between CLRMARKERS detected in a sample and background noise. Normalization methods and normalized values will differ depending on the method by which the biomarkers are detected. Preferably, mathematical algorithms can be used to combine information from results of multiple individual CLRMARKERS into a single measurement or index. Subjects identified as having an increased risk of colorectal cancer can optionally be selected to receive treatment regimens, such as administration of prophylactic or therapeutic compounds such as "colorectal cancer-modulating agents" as defined herein to prevent or delay the onset of colorectal cancer.

The amount of the CLRMARKER protein, peptide, nucleic acid, polymorphism, metabolite, or other analyte can be measured in a test sample and compared to the normal control level. The term "normal control level", means the level of one or more CLRMARKER proteins, nucleic acids, polymorphisms, metabolites, or other analytes, or CLRMARKER indices, typically found in a subject not suffering from colorectal cancer and not likely to have colorectal cancer, e.g., relative to samples collected from longitudinal studies of young subjects who were monitored until advanced age and were found not to develop colorectal cancer or related disease sequelae, such as ulcerative colitis, inflammatory bowel disease, and/or Crohn's disease. The normal control level can be a range or an index. Alternatively, the normal control level can be a database of patterns from previously tested subjects. A change in the level in the subject-derived sample of one or more CLRMARKER protein, nucleic acid, polymorphism, metabolite, or other analyte compared to the normal control level can indicate that the subject is suffering from or is at risk of developing colorectal cancer. In contrast, when the methods are applied prophylactically, a similar level compared to the normal control level in the subject-derived sample of one or more CLRMARKER proteins, nucleic acids, polymorphisms, metabolites, or other analytes can indicate that the subject is not suffering from, is not at risk or is at low risk of developing colorectal cancer.

A reference value can refer to values obtained from a control subject or population whose cancerous state is known (i.e., has been diagnosed with or identified as suffering from colorectal cancer, or has not been diagnosed with or identified as suffering from colorectal cancer). A reference value can be an index value or baseline value, such as, for example, the "normal control level" as defined herein. The reference sample or index value or baseline value may be taken or derived from one or more subjects who have been exposed to anti-cancer treatment, radiotherapy, or chemotherapy, or may be taken or derived from one or more subjects who are at low risk of developing colorectal cancer, or may be taken or derived from subjects who have shown improvements in colorectal cancer risk factors as a result of exposure to treatment. Alternatively, the reference sample or index value or baseline value may be taken or derived from one or more subjects who have not been exposed to anti-cancer treatment, radiotherapy, or chemotherapy. For example, samples may be collected from subjects who have received initial treatment for colorectal cancer and subsequent treatment for colorectal cancer to monitor the progress of the treatment. A reference value can also comprise a value derived from risk prediction algorithms or computed indices from population studies of colorectal cancer, such as those disclosed herein. A reference value can also comprise a value from subjects or populations that have developed polyps, ulcerative colitis, inflammatory bowel disease, and/or Crohn's disease without developing colorectal cancer.

Differences in the level or amounts (which can be an "effective amount") of CLRMARKERS measured by the methods of the present invention can comprise increases or decreases in the level or amounts of CLRMARKERS as compared to a normal control level, reference value, index value, or baseline value. The increase or decrease in the amounts of CLRMARKERS relative to a reference value can be indicative of progression of colorectal cancer, delay, progression, development, or amelioration of colorectal cancer, an increase or decrease in the risk of developing colorectal cancer, or complications relating thereto. The increase or decrease can be indicative of the success of one or more treatment regimens for colorectal cancer, or can indicate improvements or regression of colorectal cancer risk factors. The increase or decrease can be, for example, at least 5%, at least 10%, at least 15%, at least 20%, at least 25%, at least 30%, at least 35%, at least 40%, at least 45%, or at least 50% of the reference value or normal control level.

The difference in the level (or amounts) of CLRMARKERS is preferably statistically significant. "Statistically significant" means that the alteration is greater than what might be expected to happen by chance alone. Statistical significance can be determined by any method known in the art. For example, statistical significance can be determined by p-value. The p-value is a measure of probability that a difference between groups during an experiment happened by chance. (P(z≥zobserved)). For example, a p-value of 0.01 means that there is a 1 in 100 chance the result occurred by chance. The lower the p-value, the more likely it is that the difference between groups was caused by treatment. An alteration is considered to be statistically significant if the p-value is at least 0.05. Preferably, the p-value is 0.04, 0.03, 0.02, 0.01, 0.005, 0.001 or less. As noted below, and without any limitation of the invention, achieving statistical significance generally, but not always, requires that combinations of several CLRMARKERS be used together in panels and combined with mathematical algorithms in order to achieve a statistically significant CLRMARKER index.

The "diagnostic accuracy" of a test, assay, or method concerns the ability of the test, assay, or method to distinguish between subjects having colorectal cancer, or at risk for colorectal cancer, which is based on whether the subjects have a "clinically significant presence" or a "clinically significant alteration" in the levels of one or more CLRMARKERS. By "clinically significant presence" or "clinically significant alteration", it is meant that the presence of the CLRMARKER (e.g., mass, such as milligrams, nanograms, or mass per volume, such as milligrams per deciliter or copy number of a transcript per unit volume) or an alteration in the presence of the CLRMARKER in the subject (typically in a sample from the subject) is higher than the predetermined cut-off point (or threshold value) for that CLRMARKER and therefore indicates that the subject has colorectal cancer for which the sufficiently high presence of that protein, peptide, nucleic acid, polymorphism, metabolite or analyte is a marker.

The present invention may be used to make categorical or continuous measurements of the risk of conversion to colorectal cancer, thus diagnosing a category of subjects defined as at risk for developing colorectal cancer (such as those subjects who are diagnosed with colon or rectal polyps, or who have been diagnosed with ulcerative colitis, inflammatory bowel disease, and/or Crohn's disease). In the categorical scenario, the methods of the present invention can be used to discriminate between normal and those subjects at risk for developing colorectal cancer. In this categorical use of the invention, the terms "high degree of diagnostic accuracy" and "very high degree of diagnostic accuracy" refer to the test or assay for that CLRMARKER (or CLRMARKER index; wherein CLRMARKER value encompasses any individual measurement whether from a single CLRMARKER or derived from an index of CLRMARKERS) with the predetermined cut-off point correctly (accurately) indicating the presence or absence of a pre-colorectal cancer condition. A perfect test would have perfect accuracy. Thus, for subjects who are at risk for developing colorectal cancer, the test would indicate only positive test results and would not report any of those subjects as being "negative" (there would be no "false negatives"). In other words, the "sensitivity" of the test (the true positive rate) would be 100%. On the other hand, for subjects who are not at risk for developing colorectal cancer, the test would indicate only negative test results and would not report any of those subjects as being "positive" (there would be no "false positives"). In other words, the "specificity" (the true negative rate) would be 100%. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test. In other embodiments, the present invention may be used to discriminate those at risk of developing colorectal cancer from those who have colorectal cancer, or those who have colorectal cancer from normal subjects. Such use may require different subsets of CLRMARKERS (out of the total CLR-MARKERS as disclosed in Table 1), mathematical algorithms, and/or cut-off points, but be subject to the same aforementioned measurements of diagnostic accuracy for the intended use.

In the categorical diagnosis of a disease, changing the cut-off point or threshold value of a test (or assay) usually changes the sensitivity and specificity, but in a qualitatively inverse relationship. For example, if the cut point is lowered, more subjects in the population tested will typically have test results over the cut point or threshold value. Because subjects who have test results above the cut point are reported as having the disease, condition, or syndrome for which the test is conducted, lowering the cut point will cause more subjects to be reported as having positive results (e.g., that they have colorectal cancer). Thus, a higher proportion of those who have colorectal cancer will be indicated by the test to have it. Accordingly, the sensitivity (true positive rate) of the test will be increased. However, at the same time, there will be more false positives because more people who do not have the disease, condition, or syndrome (e.g., people who are truly "negative") will be indicated by the test to have CLR-MARKER values above the cut point and therefore to be reported as positive (e.g., to have the disease, condition, or syndrome) rather than being correctly indicated by the test to be negative. Accordingly, the specificity (true negative rate) of the test will be decreased. Similarly, raising the cut point will tend to decrease the sensitivity and increase the specificity. Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points.

A Receiver Operating Characteristics ("ROC") curve can be used as an indicator that allows representation of the sensitivity and specificity of a test, assay, or method over the entire range of test (or assay) cut points with just a single value. See, e.g., Shultz, "Clinical Interpretation Of Laboratory Procedures," chapter 14 in Teitz, Fundamentals of Clinical Chemistry, Burtis and Ashwood (eds.), 4$^{th}$ edition 1996, W.B. Saunders Company, pages 192-199; and Zweig et al., "ROC Curve Analysis: An Example Showing The Relationships Among Serum Lipid And Apolipoprotein Concentrations In Identifying Subjects With Coronary Artery Disease," Clin. Chem., 1992, 38(8): 1425-1428.

An ROC curve is an x-y plot of sensitivity on the y-axis, on a scale of zero to one (e.g., 100%), against a value equal to one minus specificity on the x-axis, on a scale of zero to one (e.g., 100%). Thus, a ROC curve is a plot of the true positive rate against the false positive rate for that test, assay, or method. To construct the ROC curve for the test, assay, or method in question, subjects can be assessed using a perfectly accurate or "gold standard" method that is independent of the test, assay, or method in question to determine whether the subjects are truly positive or negative for the disease, condition, or syndrome (for example, coronary angiography is a gold standard test for the presence of coronary atherosclerosis). The subjects can also be tested using the test, assay, or method in question, and for varying cut points, the subjects are reported as being positive or negative according to the test, assay, or method. The sensitivity (true positive rate) and the value equal to one minus the specificity (which value equals the false positive rate) are determined for each cut point, and each pair of x-y values is plotted as a single point on the x-y diagram. The "curve" connecting those points is the ROC curve. The ROC curve is often used in order to determine the optimal single clinical cut-off or treatment threshold value where sensitivity and specificity are maximized. Such a situation represents the point on the ROC curve that describes the upper left corner of the single largest rectangle which can be drawn under the curve.

The total area under the curve ("AUC") is the indicator that allows representation of the sensitivity and specificity of a test, assay, or method over the entire range of cut points with just a single value. The maximum AUC is one (a perfect test) and the minimum area is one half (e.g. the area where there is no discrimination of normal versus disease). The closer the AUC is to one, the better is the accuracy of the test. It should be noted that implicit in all ROC and AUC is the definition of the disease and the post-test time horizon of interest.

As defined herein, a "high degree of diagnostic accuracy" means a test or assay wherein the AUC (area under the ROC curve for the test or assay) is at least 0.70, preferably at least 0.75, more preferably at least 0.80, preferably at least 0.85, more preferably at least 0.90, and most preferably at least 0.95.

A "very high degree of diagnostic accuracy" means a test or assay wherein the AUC (area under the ROC curve for the test or assay) is at least 0.80, preferably at least 0.85, more preferably at least 0.875, preferably at least 0.90, more preferably at least 0.925, and most preferably at least 0.95.

Alternatively, in low disease prevalence tested populations (defined as those with less than 1% rate of occurrences per annum), ROC and AUC can be misleading as to the clinical utility of a test, and absolute and relative risk ratios as defined elsewhere in this disclosure can be employed to determine the degree of diagnostic accuracy. Populations of subjects to be tested can also be categorized into quartiles, where the top quartile (25% of the population) comprises the group of subjects with the highest relative risk for developing or suffering from colorectal cancer, and the bottom quartile comprising the group of subjects having the lowest relative risk for developing colorectal cancer. In general, values derived from tests or assays having over 2.5 times the relative risk from top to bottom quartile in a low prevalence population are considered to have a "high degree of diagnostic accuracy," and those with five to seven times the relative risk for each quartile are considered to have a very high degree of diagnostic accuracy. Nonetheless, values derived from tests or assays having only 1.2 to 2.5 times the relative risk for each quartile remain clinically useful are widely used as risk factors for a disease.

The predictive value of any diagnostic test depends on the sensitivity and specificity of the test, and on the prevalence of the condition in the population being tested. The greater the likelihood that the condition being screened for is present in a subject or in the population (pre-test probability), the greater the validity of a positive test and the greater the likelihood that the result is a true positive. Thus, the problem with using a test in any population where there is a low likelihood of the condition being present is that a positive result has limited value (i.e., more likely to be a false positive). Similarly, in populations at very high risk, a negative test result is more likely to be a false negative. By defining the degree of diagnostic accuracy, i.e., cut points on a ROC curve, defining an acceptable AUC value, and determining the acceptable ranges in relative concentration of what constitutes an effective amount of the CLRMARKERS of the invention allows one of skill in the art to use the CLRMARKERS to diagnose or identify subjects with a pre-determined level of predictability.

Alternative methods of determining diagnostic accuracy must be used with continuous measurements of risk, which are commonly used when a disease category or risk category has not yet been clearly defined by the relevant medical societies and practice of medicine.

"Risk" in the context of the present invention can mean "absolute" risk, which refers to that percentage probability that an event will occur over a specific time period. Absolute risk can be measured with reference to either actual observation post-measurement for the relevant time cohort, or with reference to index values developed from statistically valid historical cohorts that have been followed for the relevant time period. "Relative" risk refers to the ratio of absolute risks of a subject's risk compared either to low risk cohorts or average population risk, which can vary by how clinical risk factors are assessed. Odds ratios, the proportion of positive events to negative events for a given test result, are also commonly used (odds are according to the formula $p/(1-p)$ where p is the probability of event and $(1-p)$ is the probability of no event) to no-conversion. Alternative continuous measures which may be assessed in the context of the present invention include time to colorectal cancer conversion and therapeutic colorectal cancer conversion risk reduction ratios.

For such continuous measures, measures of diagnostic accuracy for a calculated index are typically based on linear regression curve fits between the predicted continuous value and the actual observed values (or historical index calculated value) and utilize measures such as R squared, p values and confidence intervals. Predicted values using such algorithms are often reported with a confidence interval (usually 90% or 95% CI) based on a historical observed cohort's predictions, as in the test for risk of future breast cancer recurrence commercialized by Genomic Health (Redwood City, Calif.).

Risk prediction for colorectal cancer can also encompass risk prediction algorithms and computed indices that assess and estimate a subject's absolute risk for developing colorectal cancer with reference to a historical cohort. Risk assessment using such predictive mathematical algorithms and computed indices has increasingly been incorporated into guidelines for diagnostic testing and treatment, and encompass indices obtained from and validated with, inter alia, multi-stage, stratified samples from a representative population. See, for example, Acute Physiology and Chronic Health Evaluation (APACHE) scoring systems, such as APACHE I, II, and III, the Simplified Acute Physiology Score (SAPS I and II), and POSSUM model systems (Cowen, J. S. and Kelley, M. A. (1994) Crit. Care Clin 10: 53; Escarce, J. J. and Kelley, M. A. (1990) JAMA 264: 2389; Knaus, W. A., Wagner, D. P., Draper, E. A., et al. (1991) Chest 100: 1619; the contents of which are incorporated herein by reference).

Despite the numerous studies and algorithms that have been used to assess the risk of colorectal cancer, the evidence-based, multiple risk factor assessment approach is only moderately accurate for the prediction of short- and long-term risk of manifesting colorectal cancer in individual asymptomatic or otherwise healthy subjects. Such risk prediction algorithms can be advantageously used in combination with the CLRMARKERS of the present invention to distinguish between subjects in a population of interest to determine the risk stratification of developing colorectal cancer. The CLRMARKERS and methods of use disclosed herein provide tools that can be used in combination with such risk prediction algorithms to assess, identify, or diagnose subjects who are asymptomatic and do not exhibit the conventional risk factors.

The data derived from risk prediction algorithms and from the methods of the present invention can be compared by linear regression. Linear regression analysis models the relationship between two variables by fitting a linear equation to observed data. One variable is considered to be an explanatory variable, and the other is considered to be a dependent variable. For example, values obtained from the APACHE population analyses can be used as a dependent variable and analyzed against levels of one or more CLRMARKERS as the explanatory variables in an effort to more fully define the underlying biology implicit in the calculated algorithm score. Alternatively, such risk prediction algorithms, or their individual inputs, which are generally CLRMARKERS themselves, can be directly incorporated into the practice of the present invention, with the combined algorithm compared against actual observed results in a historical cohort.

Linear regression analyses can be used, inter alia, to predict the risk of developing colorectal cancer based upon correlating the levels of one or more CLRMARKERS in a sample from a subject to that subjects' actual observed clinical outcomes, or in combination with, for example, calculated APACHE risk scores, SAPS scores, POSSUM risk scores, or other known methods of diagnosing or predicting the prevalence of colorectal cancer, including the compound covariate predictor (CCP) described by Tukey, J. (1993) Controlled Clinical Trials, and popularized in the microarray field by Richard Simons work, the Benjamini-Hochberg method for calculating the false discovery rate in a clinical or diagnostic assay (see, for example, Klipper-Aurbach, Y. et al., (1995) Med. Hypotheses 45(5): 486-90), the Mann-Whitney U test, the Wilcoxon test for equality of medians (see Wilcoxon, F. (1945) Biometrics, 1, 80-83), and the Hochberg method for family-wise correction (see, for example, Levin, B. (1996) Am. J. Public Health 86(5): 628-629). Of particular use, however, are non-linear equations and analyses to determine the relationship between known predictive models of colorectal cancer and levels of CLRMARKERS detected in a subject sample. Of particular interest are structural and synactic classification algorithms, and methods of risk index construction, utilizing pattern recognition features, including established techniques such as the Kth-Nearest Neighbor, Boosting, Decision Trees, Neural Networks, Bayesian Networks, Support Vector Machines, and Hidden Markov Models. Furthermore, the application of such techniques to panels of multiple CLRMARKERS is encompassed by or within the ambit of the present invention, as is the use of such combination to create single numerical "risk indices" or "risk scores" encompassing information from multiple CLRMARKER inputs.

Factor analysis can be very useful in constructing CLRMARKER panels from their constituent components, and in grouping substitutable groups of markers. Factor analysis is a mathematical technique by which a large number of correlated variables (such as colorectal cancer risk factors) can be reduced to fewer "factors" that represent distinct attributes that account for a large proportion of the variance in the original variables (see, for example, Slattery, M. L. et al., (1998) Am. J. Epidemiol. 148: 4-16; Martinez, M. E. et al., (1998) Am. J. Epidemiol. 148:17-19). Epidemiological studies of factor "scores" from these analyses can further determine relations between components of, for example, ulcerative colitis, inflammatory bowel disease, and/or Crohn's disease and incidence of colorectal cancer. The premise underlying factor analysis is that correlations observed among a set of variables can be explained by a small number of unique unmeasured variables, or "factors". Factor analysis involves two procedures: 1) factor extraction to estimate the number of factors, and 2) factor rotation to determine constituents of each factor in terms of the original variables. Factor extraction can be conducted by the method of principal components. These components are linear combinations of the original variables that are constructed so that each component has a correlation of zero with each of the other components. Each principal component is associated with an "eigen-value," which represents the variance in the original variables explained by that component (with each original variable standardized to have a variance of 1). The number of principal components that can be constructed is equal to the number of original variables. In factor analysis, the number of factors is customarily determined by retention of only those components that account for more of the total variance than any single original variable (i.e., those components with eigen-values of >1).

Once the number of factors has been established, then factor rotation is conducted to determine the composition of factors that has the most parsimonious interpretation in terms of the original variables. In factor rotation, "factor loadings," which represent correlations of each factor with the original variables, are changed so that these factor loadings are made as close to 0 or 1 as possible (with the constraint that the total amount of variance explained by the factors remains unchanged). A number of methods for factor rotation have been developed and can be distinguished by whether they require the final set of factors to remain uncorrelated with one another (also known as "orthogonal methods") or by whether they allow factors to be correlated ("oblique methods"). In interpretation of factor analysis, the pattern of factor loadings is examined to determine which original variables represent primary constituents of each factor. Conventionally, variables that have a factor loading of >0.4 (or less than −0.4) with a particular factor are considered to be its major constituents.

Comparison can be performed on test ("subject") and reference ("control") samples measured concurrently or at temporally distinct times. An example of the latter is the use of compiled expression information, e.g., a sequence database, which assembles information about expression levels of CLRMARKERS. If the reference sample, e.g., a control sample is from a subject that does not have colorectal cancer and there is a similarity in the amount of the CLRMARKERS in the subject test sample and the control reference sample, indicates that the treatment is efficacious. However, a change in the amount of one or more CLRMARKERS in the test sample and the reference sample can reflect a less favorable clinical outcome or prognosis. "Efficacious" or "effective" means that the treatment leads to an decrease or increase in the amount of one or more CLRMARKERS. Efficacy can be determined in association with any known method for diagnosing or treating colorectal cancer in a subject.

The actual measurement of levels of the CLRMARKERS of the present invention can be determined at the protein or nucleic acid level using any method known in the art. For example, at the nucleic acid level, Northern and Southern hybridization analysis, as well as ribonuclease protection assays using probes which specifically recognize one or more of these sequences can be used to determine gene expression. Alternatively, levels of biomarkers can be measured using reverse-transcription-based PCR assays (RT-PCR), e.g., using primers specific for the differentially expressed sequence of genes. Levels of biomarkers can also be determined at the protein level, e.g., by measuring the levels of peptides encoded by the gene products described herein, or activities thereof. Such methods are well known in the art and include, e.g., immunoassays based on antibodies to proteins encoded by the genes, aptamers or molecular imprints. Any biological material can be used for the detection/quantification of the protein or its activity. Alternatively, a suitable method can be selected to determine the activity of proteins encoded by the biomarker genes according to the activity of each protein analyzed.

CLRMARKER amounts can be detected, inter alia, electrophoretically (such as by agarose gel electrophoresis, sodium dodecyl sulfate-polyacrylamide gel electrophoresis (SDS-PAGE), Tris-HCl polyacrylamide gels, non-denaturing protein gels, two-dimensional gel electrophoresis (2DE), and the like), immunochemically (i.e., radioimmunoassay, immunoblotting, immunoprecipitation, immunofluorescence, enzyme-linked immunosorbent assay), by "proteomic analysis", or by "genomic analysis."

"Proteomic analysis" includes, but is not limited to, surface enhanced laser desorption ionization (SELDI), matrix-assisted laser desorption ionization-time of flight (MALDI-TOF), high performance liquid chromatography (HPLC), liquid chromatography with or without mass spectrometry (LC/MS), tandem LC/MS, protein arrays, peptide arrays, and antibody arrays.

"Genomic analysis" can comprise, for example, polymerase chain reaction (PCR), real-time PCR (such as by Light Cycler®, available from Roche Applied Sciences), serial analysis of gene expression (SAGE), Northern blot analysis, and Southern blot analysis.

Microarray technology can be used as a tool for analyzing gene or protein expression, comprising a small membrane or solid support (such as but not limited to microscope glass slides, plastic supports, silicon chips or wafers with or without fiber optic detection means, and membranes including nitrocellulose, nylon, or polyvinylidene fluoride). The solid support can be chemically (such as silanes, streptavidin, and numerous other examples) or physically derivatized (for example, photolithography) to enable binding of the analyte of interest, usually nucleic acids, proteins, or metabolites or fragments thereof. The nucleic acid or protein can be printed (i.e., inkjet printing), spotted, or synthesized in situ. Deposition of the nucleic acid or protein of interest can be achieved by xyz robotic microarrayers, which utilize automated spotting devices with very precise movement controls on the x-, y-, and z-axes, in combination with pin technology to provide accurate, reproducible spots on the arrays. The analytes of interest are placed on the solid support in an orderly or fixed arrangement so as to facilitate easy identification of a particularly desired analyte. A number of microarray formats are commercially available from, inter alia, Affymetrix, ArrayIt, Agilent Technologies, Asper Biotech, BioMicro, CombiMatrix, GenePix, Nanogen, and Roche Diagnostics.

The nucleic acid or protein of interest can be synthesized in the presence of nucleotides or amino acids tagged with one or more detectable labels. Such labels include, for example, fluorescent dyes and chemiluminescent labels. In particular, for microarray detection, fluorescent dyes such as but not limited to rhodamine, fluorescein, phycoerythrin, cyanine dyes like Cy3 and Cy5, and conjugates like streptavidin-phycoerythrin (when nucleic acids or proteins are tagged with biotin) are frequently used. Detection of fluorescent signals and image acquisition are typically achieved using confocal fluorescence laser scanning or photomultiplier tube, which provide relative signal intensities and ratios of analyte abundance for the nucleic acids or proteins represented on the array. A wide variety of different scanning instruments are available, and a number of image acquisition and quantification packages are associated with them, which allow for numerical evaluation of combined selection criteria to define optimal scanning conditions, such as median value, interquartile range (IQR), count of saturated spots, and linear regression between pair-wise scans (r2 and P). Reproducibility of the scans, as well as optimization of scanning conditions, background correction, and normalization, are assessed prior to data analysis.

Normalization refers to a collection of processes that are used to adjust data means or variances for effects resulting from systematic non-biological differences between arrays, subarrays (or print-tip groups), and dye-label channels. An array is defined as the entire set of target probes on the chip or solid support. A subarray or print-tip group refers to a subset of those target probes deposited by the same print-tip, which can be identified as distinct, smaller arrays of proves within the full array. The dye-label channel refers to the fluorescence frequency of the target sample hybridized to the chip. Experiments where two differently dye-labeled samples are mixed and hybridized to the same chip are referred to in the art as "dual-dye experiments", which result in a relative, rather than absolute, expression value for each target on the array, often represented as the log of the ratio between "red" channel and "green channel." Normalization can be performed according to ratiometric or absolute value methods. Ratiometric analyses are mainly employed in dual-dye experiments where one channel or array is considered in relation to a common reference. A ratio of expression for each target probe is calculated between test and reference sample, followed by a transformation of the ratio into log 2(ratio) to symmetrically represent relative changes. Absolute value methods are used frequently in single-dye experiments or dual-dye experiments where there is no suitable reference for a channel or array. Relevant "hits" are defined as expression levels or amounts that characterize a specific experimental condition. Usually, these are nucleic acids or proteins in which the expression levels differ significantly between different experimental conditions, usually by comparison of the expression levels of a nucleic acid or protein in the different conditions and analyzing the relative expression ("fold change") of the nucleic acid or protein and the ratio of its expression level in one set of samples to its expression in another set.

Data obtained from microarray experiments can be analyzed by any one of numerous statistical analyses, such as clustering methods and scoring methods. Clustering methods attempt to identify targets (such as nucleic acids and/or proteins) that behave similarly across a range of conditions or samples. The motivation to find such targets is driven by the assumption that targets that demonstrate similar patterns of expression share common characteristics, such as common regulatory elements, common functions, or common cellular origins.

Hierarchical clustering is an agglomerative process in which single-member clusters are fused to bigger and bigger clusters. The procedure begins by computing a pairwise distance matrix between all the target molecules, the distance matrix is explored for the nearest genes, and they are defined as a cluster. After a new cluster is formed by agglomeration of two clusters, the distance matrix is updated to reflect its distance from all other clusters. Thereafter, the procedure searches for the nearest pair of clusters to agglomerate, and so on. This procedure results in a hierarchical dendrogram in which multiple clusters are fused to nodes according to their similarity, resulting in a single hierarchical tree. Hierarchical clustering software algorithms include, for example, Cluster and Treeview.

K-means clustering is an iterative procedure that searches for clusters that are defined in terms of their "center" points or means. Once a set of cluster centers is defined, each target molecule is assigned to the cluster it is closest to. The clustering algorithm then adjusts the center of each cluster of genes to minimize the sum of distances of target molecules in each cluster to the center. This results in a new choice of cluster centers, and target molecules can be reassigned to clusters. These iterations are applied until convergence is observed. Self-organizing maps (SOMs) are related in part to the k-means procedure, in that the data is assigned to a predetermined set of clusters. However, unlike k-means, what follows is an iterative process in which gene expression vectors in each cluster are "trained" to find the best distinctions between the different clusters. In other words, a partial structure is imposed on the data and then this structure is iteratively modified according to the data. SOM is included in many software packages, such as, for instance, GeneCluster. Other clustering methods include graph-theoretic clustering, which utilizes graph-theoretic and statistical techniques to identify tight groups of highly similar elements (kernels), which are likely to belong to the same true cluster. Several heuristic procedures are then used to expand the kernels into the full clustering. An example of software utilizing graph-theoretic clustering includes CLICK in combination with the Expander visualization tool.

Data obtained from high-throughput expression analyses can be scored using statistical methods such as parametric and non-parametric methods. Parametric approaches model expression profiles within a parametric representation and ask how different the parameters of the experimental groups are. Examples of parametric methods include, without limitation, t-tests, separation scores, and Bayesian t-tests. Non-parametric methods involve analysis of the data, wherein no a priori assumptions are made about the distribution of expression profiles in the data, and the degree to which the two groups of expression measurements are distinguished is directly examined. Another method uses the TNOM, or the threshold number of misclassifications, which measures the success in separation two groups of samples by a simple threshold over the expression values.

SAGE (serial analysis of gene expression) can also be used to systematically determine the levels of gene expression. In SAGE, short sequence tags within a defined position containing sufficient information to uniquely identify a transcript are used, followed by concatenation of tags in a serial fashion. See, for example, Velculescu V. E. et al, (1995) Science 270: 484-487. Polyadenylated RNA is isolated by oligo-dT priming, and cDNA is then synthesized using a biotin-labeled primer. The cDNA is subsequently cleaved with an anchoring restriction endonucleases, and the 3'-terminal cDNA fragments are bound to streptavidin-coated beads. An oligonucleotide linker containing recognition sites for a tagging enzyme is linked to the bound cDNA. The tagging enzyme can be a class II restriction endonucleases that cleaves the DNA at a constant number of bases 3' to the recognition site, resulting in the release of a short tag and the linker from the beads after digestion with the enzyme. The 3' ends of the released tags plus linkers are then blunt-ended and ligated to one another to form linked ditags that are approximately 100 base pairs in length. The ditags are then subjected to PCR amplification, after which the linkers and tags are released by digestion with the anchoring restriction endonucleases. Thereafter, the tags (usually ranging in size from 25-30-mers) are gel purified, concatenated, and cloned into a sequence vector. Sequencing the concatemers enables individual tags to be identified and the abundance of the transcripts for a given cell or tissue type can be determined.

Of particular utility are two-dimensional gel electrophoresis, which separates a mixture of proteins (such as found in biological samples such as serum) in one dimension according to the isoelectric point (such as, for example, a pH range from 5-8), and according to molecular weight in a second dimension. Two-dimensional liquid chromatography can also be advantageously used to identify or detect CLRMARKER proteins, polypeptides, mutations, and polymorphisms of the invention.

CLRMARKER proteins, polypeptides, mutations, and polymorphisms can be typically detected by contacting a sample from the subject with an antibody which binds the CLRMARKER protein, polypeptide, mutation, or polymorphism and then detecting the presence or absence of a reaction product. The antibody may be monoclonal, polyclonal, chimeric, or a fragment of the foregoing, as discussed in detail herein, and the step of detecting the reaction product may be carried out with any suitable immunoassay. The isolated antibody can comprise, for example, a human constant region (as defined herein) and an antigen-binding region that binds to one or more CLRMARKERS set forth in Table 1, preferably at least one, preferably two, three, four, five, six, seven, eight, nine, ten or more amino acid residues. The sample from the subject is typically a biological fluid as defined by the term "sample" above, and may be the same sample of biological fluid used to conduct the method described above.

Immunoassays carried out in accordance with the present invention may be homogeneous assays or heterogeneous assays. In a homogeneous assay, the immunological reaction usually involves the specific antibody (e.g., anti-CLRMARKER protein antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A agarose, protein G agarose, latex, polystyrene, magnetic or paramagnetic beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are oligonucleotides, immunoblotting, immunoprecipitation, immunofluorescence methods, chemiluminescence methods, electrochemiluminescence or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label."

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., $^{35}S$, $^{125}I$, $^{131}I$), enzyme labels (e.g., horseradish peroxidase, alkaline phosphatase), and fluorescent labels (e.g., fluorescein, Alexa, green fluorescent protein) in accordance with known techniques.

Antibodies can also be useful for detecting post-translational modifications of CLRMARKER proteins, polypeptides, mutations, and polymorphisms, such as tyrosine phosphorylation, threonine phosphorylation, serine phosphorylation, glycosylation (e.g., O-GlcNAc). Such antibodies specifically detect the phosphorylated amino acids in a protein or proteins of interest, and can be used in immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF) (Wirth, U. et al. (2002) Proteomics 2(10): 1445-51).

For CLRMARKER proteins, polypeptides, mutations, and polymorphisms known to have enzymatic activity, the activities can be determined in vitro using enzyme assays known in the art. Such assays include, without limitation, kinase assays, phosphatase assays, reductase assays, among many others. Modulation of the kinetics of enzyme activities can be determined by measuring the rate constant KM using known algorithms, such as the Hill plot, Michaelis-Menten equation, linear regression plots such as Lineweaver-Burk analysis, and Scatchard plot.

Expression of the genes disclosed herein can be measured at the RNA level using any method known in the art. For example, Northern hybridization analysis using probes which specifically recognize one or more of these sequences can be used to determine gene expression. Alternatively, expression can be measured using reverse-transcription-based PCR assays (RT-PCR), e.g., using primers specific for the differentially expressed sequences.

Alternatively, CLRMARKER protein and nucleic acid metabolites or fragments can be measured. The term "metabolite" includes any chemical or biochemical product of a metabolic process, such as any compound produced by the processing, cleavage or consumption of a biological molecule (e.g., a protein, nucleic acid, carbohydrate, or lipid). Metabolites can be detected in a variety of ways known to one of skill in the art, including the refractive index spectroscopy (RI), ultra-violet spectroscopy (UV), fluorescence analysis, radiochemical analysis, near-infrared spectroscopy (near-IR), nuclear magnetic resonance spectroscopy (NMR), light scattering analysis (LS), mass spectrometry, pyrolysis mass spectrometry, nephelometry, dispersive Raman spectroscopy, gas chromatography combined with mass spectrometry, liquid chromatography combined with mass spectrometry, matrix-assisted laser desorption ionization-time of flight (MALDI-TOF) combined with mass spectrometry, surface-enhanced laser desorption ionization (SELDI), ion spray spectroscopy combined with mass spectrometry, capillary electrophoresis, NMR and IR detection. (See, WO 04/056456 and WO 04/088309, each of which are hereby incorporated by reference in their entireties) In this regard, other CLRMARKER analytes can be measured using the above-mentioned detection methods, or other methods known to the skilled artisan.

Using sequence information provided by the database entries for the biomarker sequences, expression of the biomarker sequences can be detected (if present) and measured using techniques well known to one of ordinary skill in the art. For example, sequences within the sequence database entries corresponding to biomarker sequences, or within the sequences disclosed herein, can be used to construct probes for detecting biomarker RNA sequences in, e.g., Northern blot hybridization analyses or methods which specifically, and, preferably, quantitatively amplify specific nucleic acid sequences. As another example, the sequences can be used to construct primers for specifically amplifying the biomarker sequences in, e.g., amplification-based detection methods such as reverse-transcription based polymerase chain reaction (RT-PCR). When alterations in gene expression are associated with gene amplification, deletion, polymorphisms, and mutations, sequence comparisons in test and reference populations can be made by comparing relative amounts of the examined DNA sequences in the test and reference cell populations.

Expression of the genes disclosed herein can be measured at the RNA level using any method known in the art. For example, Northern hybridization analysis using probes which specifically recognize one or more of these sequences can be used to determine gene expression. Alternatively, expression can be measured using reverse-transcription-based PCR assays (RT-PCR), e.g., using primers specific for the differentially expressed sequences. RNA can also be quantified using, for example, other target amplification methods (e.g., TMA, SDA, NASBA), or signal amplification methods (e.g., bDNA), and the like. Preferably, levels of expression of the biomarkers of the present invention are detected by real-time PCR, as described further in PCT/US02/38806 (published as WO03/048377, and Therianos et al., (2004) Am. J. Pathol. 164(3): 795-806, the contents of which are incorporated in their entireties herein by reference).

Levels of an effective amount of CLRMARKER proteins, peptides, nucleic acids, polymorphisms, metabolites, or other analytes also allows for the course of treatment of colorectal cancer to be monitored. In this method, a biological sample can be provided from a subject undergoing treatment regimens, e.g., drug treatments, for colorectal cancer. Such treatment regimens can include, but are not limited to, dietary supplementation (including without limitation, alpha-lipoic acid, chromium, coenzyme Q10, garlic, magnesium, and omega-3 fatty acids), surgical intervention (such as but not limited to colorectal resection, etc.), and treatment with therapeutics or prophylactics used in subjects diagnosed or identified with colorectal cancer, such as for example, colorectal cancer-modulating agents as defined herein. If desired, biological samples are obtained from the subject at various time points before, during, or after treatment. Levels of an effective amount of CLRMARKER proteins, peptides, nucleic acids, polymorphisms, metabolites, or other analytes can then be determined and compared to a reference value, e.g. a control subject or population whose cancer state is known or an index value or baseline value. The reference sample or index value or baseline value may be taken or derived from one or more subjects who have been exposed to the treatment, or may be taken or derived from one or more subjects who are at low risk of developing colorectal cancer, or may be taken or derived from subjects who have shown improvements in colorectal cancer risk factors as a result of exposure to treatment. Alternatively, the reference sample or index value or baseline value may be taken or derived from one or more subjects who have not been exposed to the treatment. For example, samples may be collected from subjects who have received initial treatment for colorectal cancer and subsequent treatment for colorectal cancer to monitor the progress of the treatment. A reference value can also comprise a value derived from risk prediction algorithms or computed indices from population studies such as those disclosed herein.

The CLRMARKERS of the present invention can thus be used to generate a "reference expression profile" which comprises a pattern of expression levels of CLRMARKERS detected in those subjects who do not have colorectal cancer, and would not be expected to develop colorectal cancer. The CLRMARKERS disclosed herein can also be used to generate a "subject expression profile" comprising a pattern of expression levels of CLRMARKERS taken from subjects who have colorectal cancer. The subject expression profiles can be compared to a reference expression profile to diagnose or identify subjects at risk for developing colorectal cancer, to monitor the progression of disease, as well as the rate of progression of disease, including development or risk of development of complications related to colorectal cancer, and to monitor the effectiveness of colorectal cancer treatment modalities.

The reference and subject expression profiles of the present invention can be contained in a machine-readable medium, such as but not limited to, analog tapes or digital media like those readable by a VCR, CD-ROM, DVD-ROM, USB flash media, among others. Such machine-readable media can also contain additional test results, such as, without limitation, measurements of conventional colorectal cancer risk factors like family history of colon and/or rectal cancer, a diet high in fat, formation of colorectal polyps, or development of ulcerative colitis, inflammatory bowel disease, and/or Crohn's disease. Alternatively or additionally, the machine-readable media can also comprise subject information such as medical history and any relevant family history. The machine-readable media can also contain information relating to other colorectal cancer-risk algorithms and computed indices such as those described herein.

Differences in the genetic makeup of subjects can result in differences in their relative abilities to metabolize various agents, which may modulate the symptoms or risk factors of colorectal cancer. Subjects that have colorectal cancer, or at risk for developing colorectal cancer can vary in age, ethnicity, diet, presence or absence of polyps, and other parameters. Accordingly, use of the CLRMARKERS disclosed herein allow for a pre-determined level of predictability that a putative therapeutic or prophylactic to be tested in a selected subject will be suitable for treating or preventing colorectal cancer, or complications thereof in the subject.

To identify therapeutics or agents that are appropriate for a specific subject, a test sample from the subject can be exposed to a therapeutic agent or a drug, and the level of one or more of CLRMARKER proteins, nucleic acids, polymorphisms, metabolites or other analytes can be determined. The level of one or more CLRMARKERS can be compared to a sample derived from the subject at a first period of time before and at a second period of time after treatment or exposure to a therapeutic agent or a drug, or can be compared to samples derived from one or more subjects who have shown improvements in colorectal cancer risk factors as a result of such treatment or exposure. Examples of such therapeutics or agents frequently used in colorectal treatments, and may modulate the symptoms or risk factors of colorectal cancer include, but are not limited to, one or more of an alkylating agent, an antibiotic agent, an antimetabolic agent, a hormonal agent, a plant-derived agent, a retinoid agent, a tyrosine kinase inhibitor, a biologic agent, a gene therapy agent, a histone deacetylase inhibitor, other anti-cancer agent, or any combination thereof. Such therapeutics or agents have been prescribed for subjects diagnosed with colorectal cancer, and may modulate the symptoms or risk factors of colorectal cancer (herein, "colorectal cancer-modulating agents").

Histone deacetylase (HDAC) inhibitors suitable for use in the present invention, include but are not limited to hydroxamic acid derivatives, Short Chain Fatty Acids (SCFAs), cyclic tetrapeptides, benzamide derivatives, or electrophilic ketone derivatives, as defined herein. Specific non-limiting examples of HDAC inhibitors suitable for use in the methods of the present invention include hydroxamic acid-containing compounds such as SAHA, Pyroxamide, CBHA, Trichostatin A (TSA), Trichostatin C, Sal icylbishydroxamic Acid, Azelaic Bishydroxamic Acid (ABHA), Azelaic-1-Hydroxamate-9-Anilide (AAHA), 6-(3-Chlorophenylureido) carpoic Hydroxamic Acid (3C1-UCHA), Oxamflatin, A-161906, Scriptaid, PXD-101, LAQ-824, CHAP, MW2796, and MW2996; cyclic tetrapeptides selected from Trapoxin A, FR901228 (FK 228 or Depsipeptide), FR225497, Apicidin, CHAP, HC-Toxin, WF27082, and Chlamydocin; short chain fatty acids (SCFAs) selected from Sodium Butyrate, Isovalerate, Valerate, 4 Phenylbutyrate (4-PBA), Phenylbutyrate (PB), Propionate, Butyramide, Isobutyramide, Phenylacetate, 3-Bromopropionate, Tributyrin, Valproic Acid and Valproate; benzamide derivatives such as CI-994, MS-27-275 (MS-275) and a 3'-amino derivative of MS-27-275; electrophilic ketone derivatives such as a trifluoromethyl ketone and an a-keto amide such as an N-methyl-a-ketoamide; and other miscellaneous HDAC inhibitors including natural products, psammaplins and Depudecin.

Examples of alkylating agents include, but are not limited to, bischloroethylamines (nitrogen mustards, e.g., Chlorambucil, Cyclophosphamide, Ifosfamide, Mechlorethamine, Melphalan, uracil mustard), aziridines (e.g., Thiotepa), alkyl alkone sulfonates (e.g., Busulfan), nitrosoureas (e.g., Carmustine, Lomustine, Streptozocin), nonclassic alkylating agents (Altretamine, Dacarbazine, and Procarbazine), platinum compounds (Carboplatin, Oxaliplatin, Satraplatin, and Cisplatin). These compounds react with phosphate, amino, hydroxyl, sulfihydryl, carboxyl, and imidazole groups. Other platinum compounds include those disclosed in U.S. Pat. No. 6,894,049, U.S. Pat. No. 5,244,919, and U.S. Pat. No. 5,072,011, which are hereby incorporated by reference.

Under physiological conditions, these drugs ionize and produce positively charged ions that attach to susceptible nucleic acids and proteins, leading to cell cycle arrest and/or cell death. The alkylating agents are cell cycle phase nonspecific agents because they exert their activity independently of the specific phase of the cell cycle. The nitrogen mustards and alkyl alkone sulfonates are most effective against cells in the G1 or M phase. Nitrosoureas, nitrogen mustards, and aziridines impair progression from the G1 and S phases to the M phases. Chabner and Collins eds. (1990) "Cancer Chemotherapy: Principles and Practice", Philadelphia: JB Lippincott.

Antibiotics (e.g., cytotoxic antibiotics) act by directly inhibiting DNA or RNA synthesis and are effective throughout the cell cycle. Examples of antibiotic agents include anthracyclines (e.g., Doxorubicin, Daunorubicin, Epirubicin, Idarubicin, and Anthracenedione), Mitomycin C, Bleomycin, Dactinomycin, Plicatomycin. These antibiotic agents interfere with cell growth by targeting different cellular components. For example, anthracyclines are generally believed to interfere with the action of DNA topoisomerase II in the regions of transcriptionally active DNA, which leads to DNA strand scissions.

Antimetabolic agents (i.e., antimetabolites) are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Antimitotic agents are included in this group. Examples of antimetabolic agents include, but are not limited to, Fluorouracil (5-FU), Floxuridine (5-FUdR), Methotrexate, Leucovorin, Hydroxyurea, Thioguanine (6-TG), Mercaptopurine (6-MP), Cytarabine, Pentostatin, Fludarabine Phosphate, Cladribine (2-CDA), Azacitidine, Asparaginase, Gemcitabine, Bortezomib, Flavopiridol, and Pemetrexed.

The hormonal agents are a group of drug that regulate the growth and development of their target organs. Most of the hormonal agents are sex steroids and their derivatives and analogs thereof, such as estrogens, progestogens, anti-estrogens, androgens, anti-androgens and progestins. These hormonal agents may serve as antagonists of receptors for the sex steroids to down regulate receptor expression and transcription of vital genes. Examples of such hormonal agents are synthetic estrogens (e.g., Diethylstibestrol), antiestrogens (e.g., Tamoxifen, Toremifene, Fluoxymesterol, and Raloxifene), antiandrogens (e.g., Bicalutamide, Nilutamide, and Flutamide), aromatase inhibitors (e.g., Aminoglutethimide, Anastrozole, and Tetrazole), luteinizing hormone release hormone (LHRH) analogues, Prednisone, Ketoconazole, Goserelin Acetate, Leuprolide, Megestrol Acetate, and Mifepristone. Hormonal agents are used to treat breast cancer, prostate cancer, melanoma, and meningioma. Because the major action of hormones is mediated through steroid receptors, 60% receptor-positive breast cancer responded to first-line hormonal therapy; and less than 10% of receptor-negative tumors responded. The main side effect associated with hormonal agents is flare. The frequent manifestations are an abrupt increase of bone pain, erythema around skin lesions, and induced hypercalcemia.

Specifically, progestogens are used to treat endometrial cancers, since these cancers occur in women that are exposed to high levels of estrogen unopposed by progestogen. Antiandrogens are used primarily f to decrease levels of testosterone, and thereby inhibit growth of the tumor. Hormonal treatment of breast cancer involves reducing the level of estrogen-dependent activation of estrogen receptors in neoplastic breast cells. Anti-estrogens act by binding to estrogen receptors and prevent the recruitment of coactivators, thus inhibiting the estrogen signal. LHRH analogues are used in the treatment of prostate cancer to decrease levels of testosterone and so decrease the growth of the tumor. Aromatase inhibitors act by inhibiting the enzyme required for hormone synthesis.

Plant-derived agents are a group of drugs that are derived from plants or modified based on the molecular structure of the agents. They inhibit cell replication by preventing the assembly of the cell's components that are essential to cell division. Plant-derived agents are used to treat many forms of cancer. For example, Vincristine is used in the treatment of the leukemias, Hodgkin's and non-Hodgkin's lymphoma, and the childhood tumors neuroblastoma, rhabdomyosarcoma, and Wilms' tumor. Vinblastine is used against the lymphomas, testicular cancer, renal cell carcinoma, mycosis fungoides, and Kaposi's sarcoma. Doxetaxel has shown promising activity against advanced breast cancer, non-small cell lung cancer (NSCLC), and ovarian cancer. Etoposide is active against a wide range of neoplasms, of which small cell lung cancer, testicular cancer, and NSCLC are most responsive.

Examples of plant derived agents include vinca alkaloids (e.g., Vincristine, Vinblastine, Vindesine, Vinzolidine, and Vinorelbine), podophyllotoxins (e.g., Etoposide (VP-16) and Teniposide (VM-26)), and taxanes (e.g., Paclitaxel and Docetaxel). These plant-derived agents generally act as antimitotic agents that bind to tubulin and inhibit mitosis. Podophyllotoxins such as Etoposide are believed to interfere with DNA synthesis by interacting with topoisomerase II, leading to DNA strand scission. Vincristine (e.g., Vincristine sulfate, Gensia Sicor Pharmaceuticals, Irvine, Calif.) is an alkaloid obtained from a common flowering herb, the periwinkle plant (*Vinca rosea* Linn). Vincristine sulfate is vincaleukoblastine, 22-oxo-, sulfate (1:1) (salt). Etoposide (e.g., VePesid®, Bristol-Myers Squibb Co., Princeton, N.J., also commonly known as VP-16) is a semisynthetic derivative of podophyllotoxin. The chemical name for Etoposide phosphate is 4'-demethylepipodophyllotoxin 9-[4,6-O—(R)-ethylidene-b-D-glucopyranoside], 4'-(dihydrogen phosphate). The chemical name for Etoposide is 4'-demethylepipodophyllotoxin 9-[4,6-O—(R)-ethylidene-b-D-glucopyranoside].

Other colorectal-cancer modulating agents can comprise treatment by immunotherapy with antibodies and reagents used in tumor vaccination approaches. The primary drugs in this therapy class are antibodies, alone or carrying e.g. toxins or chemotherapeutics/cytotoxics to cancer cells. Monoclonal antibodies against tumor antigens are antibodies elicited against antigens expressed by tumors, preferably tumor-specific antigens. For example, monoclonal antibody Herceptin (trastuzumab) is raised against human epidermal growth factor receptor 2 (HER2) that is overexpressed in some breast tumors including metastatic breast cancer. Overexpression of HER2 protein is associated with more aggressive disease and poorer prognosis in the clinic. Herceptin is used as a single agent for the treatment of patients with metastatic breast cancer whose tumors over express the HER2 protein.

Another example of monoclonal antibodies against tumor antigens is Rituxan (rituximab) that is raised against CD20 on lymphoma cells and selectively deplete normal and malignant CD20+ pre-B and mature B cells. Rituxan has been used as single agent for the treatment of patients with, for example, relapsed or refractory low-grade or follicular, CD20+, B cell non-Hodgkin's lymphoma. Myelotarg (gemtuzumab ozogamicin) and Campath (alemtuzumab) are further examples of monoclonal antibodies against tumor antigens that may be used.

Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle checkpoints and resulting in a higher rate of controlled cell growth-cancer. Examples of the tumor suppressor genes include Duc-4, NF-1, NF-2, RB, p53, WT1, BRCA1 and BRCA2.

Cancer vaccines are a group of agents that induce the body's specific immune response to tumors. Most of cancer vaccines under research and development and clinical trials are tumor-associated antigens (TAAs). TAAs are structures (i.e., proteins, enzymes or carbohydrates) that are present on tumor cells and relatively absent or diminished on normal cells. By virtue of being fairly unique to the tumor cell, TAAs provide targets for the immune system to recognize and cause their destruction. Examples of TAAs include gangliosides (GM2), prostate specific antigen (PSA), a-fetoprotein (AFP), carcinoembryonic antigen (CEA) (produced by colon cancers and other adenocarcinomas, e.g., breast, lung, gastric, and pancreatic cancers), melanoma-associated antigens (MART-1, gap100, MAGE 1,3 tyrosinase), papillomavirus E6 and E7 fragments, whole cells or portions/lysates of autologous tumor cells and allogeneic tumor cells.

Retinoids or retinoid agents for use with the invention include all natural, recombinant, and synthetic derivatives or mimetics of vitamin A, for example, retinyl palmitate, retinoyl-beta-glucuronide (vitamin A1 beta-glucuronide), retinyl phosphate (vitamin A1 phosphate), retinyl esters, 4-oxoretinol, 4-oxoretinaldehyde, 3-dehydroretinol (vitamin A2), 11-cis-retinal (11-cis-retinaldehyde, 11-cis or neo b vitamin A1 aldehyde), 5,6-epoxyretinol (5,6-epoxy vitamin A1 alcohol), anhydroretinol (anhydro vitamin A1) and 4-ketoretinol (4-keto-vitamin A1 alcohol), all-trans retinoic acid (ATRA; Tretinoin; vitamin A acid; 3,7-dimethyl-9-(2,6,6,-trimethyl-1-cyclohenen-1-yl)-2,4,6,8-nonatetraenoic acid [CAS No. 302-79-4]), lipid formulations of all-trans retinoic acid (e.g., ATRA-IV), 9-cis retinoic acid (9-cis-RA; Alitretinoin; Panretin©; LGD1057), (e)-4-[2-(5,6,7,8-tetrahydro-2-naphthalenyl)-1-propenyl]-benzoic acid, 3-methyl-(E)-4-[2-(5,6,7,8-tetrahydro-2-naphthalenyl)-1-propenyl]-benzoic acid, Fenretinide (N-(4-hydroxyphenyl)retinamide; 4-HPR), Etretinate (2,4,6,8-nonatetraenoic acid), Acitretin (Ro 10-1670), Tazarotene (ethyl 6-[2-(4,4-dimethylthiochroman-6-yl)-ethynyl]nicotinate), Tocoretinate (9-cis-tretinoin tocoferil), Adapalene (6-[3-(1-adamantyl)-4-methoxyphenyl]-2-naphthoic acid), Motretinide (trimethylmethoxyphenyl-N-ethyl retinamide), and retinaldehyde.

Also included as retinoids are retinoid related molecules such as CD437 (also called 6-[3-(1-adamantyl)-4-hydroxphenyl]-2-naphthalene carboxylic acid and AHPN), CD2325, ST1926 ([E-3-(4'-hydroxy-3'-adamantylbiphenyl-4-yl)acrylic acid), ST1878 (methyl 2-[3-[2-[3-(2-methoxy-1,1-dimethyl-2-oxoethoxy)phenoxy]ethoxy]phenoxy]isobutyrate), ST2307, ST1898, ST2306, ST2474, MM11453, MM002 (3-Cl-AHPC), MX2870-1, MX3350-1, MX84, and MX90-1 (Garattini et al., 2004, *Curr. Pharmaceut. Design* 10:433-448; Garattini and Terao, 2004, *J. Chemother.* 16:70-73). Included for use with the invention are retinoid agents that bind to one or more RXR. Also included are retinoid agents that bind to one or more RXR and do not bind to one or more RAR (i.e., selective binding to RXR; rexinoids), e.g., docosahexanoic acid (DHA), phytanic acid, methoprene acid, LG100268 (LG268), LG100324, LGD1057, SR 11203, SR11217, SR11234, SR11236, SR11246, AGN194204 (see, e.g., Simeone and Tari, 2004, *Cell Mol. Life. Sci.* 61:1475-1484; Rigas and Dragnev, 2005, *The Oncologist* 10:22-33; Ahuja et al., 2001, *Mol. Pharmacol.* 59:765-773; Gorgun and Foss, 2002, *Blood* 100:1399-1403; Bischoff et al., 1999, *J. Natl. Cancer Inst.* 91:2118-2123; Sun et al., 1999, *Clin. Cancer Res.* 5:431-437; Crow and Chandraratna, 2004, *Breast Cancer Res.* 6:R546-R555). Further included are derivatives of 9-cis-RA. Particularly included are 3-methyl TTNEB and related agents, e.g., Targretin®; Bexarotene; LGD1069; 4-[1-(5,6,7,8-tetrahydro-3,5,5,8,8-pentamethyl-2-naphthalenyl) ethenyl]benzoic acid, or a pharmaceutically acceptable salt or hydrate thereof.

Tyrosine kinase inhibitors for use with the invention include all natural, recombinant, and synthetic agents that decrease the activity or levels of one or more tyrosine kinases (for example, receptor tyrosine kinases), e.g., EGFR (ErbB-1; HER-1), HER-2/neu (ErbB-2), HER-3 (ErbB-3), HER-4 (ErbB-4), discoidin domain receptor (DDR), ephrin receptor (EPHR), fibroblast growth factor receptor (FGFR), hepatocyte growth factor receptor (HGFR), insulin receptor (INSR), leukocytetyrosine kinase (Ltk/Alk), muscle-specific kinase (Musk), transforming growth factor receptor (e.g., TGF-beta-RI and TGF-beta-RII), platelet-derived growth factor receptor (PDGFR), and vascular endothelial growth factor receptor (VEGFR). Inhibitors include endogenous or modified ligands for receptor tyrosine kinases such as epidermal growth factors (e.g., EGF), nerve growth factors (e.g., NGF-alpha, NGF-beta, NGF-gamma), heregulins (e.g., HRG-alpha, HRG-beta), transforming growth factors (e.g., TGF-alpha, TGF-beta), epiregulins (e.g., EP), amphiregulins (e.g., AR), betacellulins (e.g., BTC), heparin-binding EGF-like growth factors (e.g., HB-EGF), neuregulins (e.g., NRG-1, NRG-2, NRG-4, NRG-4, also called glial growth factors), acetycholine receptor-inducing activity (ARIA), and sensory motor neuron-derived growth factors (SMDGF).

Examples of inhibitors of EGFR are, e.g., Cetuximab (Erbitux; IMC-C225; MoAb C225) and Gefitinib (IRESSA™; ZD1839; ZD1839; 4-(3-chloro-4-fluoroanilino)-7-methoxy-6-(3-morpholino propoxy)quinazoline), ZD6474 (AZD6474), and EMD-72000 (Matuzumab), Panitumab (ABX-EGF; MoAb ABX-EGF), ICR-62 (MoAb ICR-62), CI-1033 (PD183805; N-[-4-[(3-Chloro-4-fluorophenyl) amino]-7-[3-(4-morpholinyl)propoxy]-6-quinazolinyl]-2-propenamide), Lapatinib (GW572016), AEE788 (pyrrolo-pyrimidine; Novartis), EKB-569 (Wyeth-Ayerst), and EXEL 7647/EXEL 09999 (EXELIS). Also included are Erlotinib and derivatives, e.g., Tarceva®; NSC 718781, CP-358774, OSI-774, R1415; N-(3-ethynylphenyl)-6,7-bis(2-methoxy-ethoxy)-4-quinazolinamine, or pharmaceutically acceptable salts or hydrates thereof (e.g., methanesulfonate salt, monohydrochloride).

Recent developments have introduced therapies for the treatment of cancer, in addition to the traditional cytotoxic and hormonal therapies used to treat cancer. For example, many forms of gene therapy are undergoing preclinical or clinical trials. In addition, approaches are currently under development that are based on the inhibition of tumor vascularization (i.e., angiogenesis). These approaches have been used to cut off the tumor from nutrition and oxygen supply provided by a newly built tumor vascular system. In addition, cancer therapy is also being attempted by the induction of terminal differentiation of the neoplastic cells. Suitable differentiation agents include the compounds disclosed in any one or more of the following references, the contents of which are incorporated by reference herein.

Polar compounds (Marks et al. (1987);, Friend, C., Scher, W., Holland, J. W., and Sato, T. (1971) *Proc. Natl. Acad. Sci.* (*USA*) 68: 378-382; Tanaka, M., Levy, J., Terada, M., Breslow, R., Rifkind, R. A., and Marks, P. A. (1975) *Proc. Natl. Acad. Sci.* (*USA*) 72: 1003-1006; Reuben, R. C., Wife, R. L., Breslow, R., Rifkind, R. A., and Marks, P. A. (1976) *Proc. Natl. Acad. Sci.* (*USA*) 73: 862-866); Derivatives of vitamin D and retinoic acid (Abe, E., Miyaura, C., Sakagami, H., Takeda, M., Konno, K., Yamazaki, T., Yoshika, S., and Suda, T. (1981) *Proc. Natl. Acad. Sci.* (*USA*) 78: 4990-4994; Schwartz, E. L., Snoddy, J. R., Kreutter, D., Rasmussen, H., and Sartorelli, A. C. (1983) *Proc. Am. Assoc. Cancer Res.* 24: 18; Tanenaga, K., Hozumi, M., and Sakagami, Y. (1980) *Cancer Res.* 40: 914-919); Steroid hormones (Lotem, J. and Sachs, L. (1975) *Int. J. Cancer* 15: 731-740); Growth factors (Sachs, L. (1978) *Nature* (Lond.) 274: 535, Metcalf, D. (1985) *Science,* 229: 16-22); Proteases (Scher, W., Scher, B. M., and Waxman, S. (1983) *Exp. Hematol.* 11: 490-498; Scher, W., Scher, B. M., and Waxman, S. (1982) *Biochem. & Biophys. Res. Comm.* 109: 348-354); Tumor promoters (Huberman, E. and Callaham, M. F. (1979) *Proc. Natl. Acad. Sci.* (*USA*) 76: 1293-1297; Lottem, J. and Sachs, L. (1979) *Proc. Natl. Acad. Sci.* (*USA*) 76: 5158-5162); and Inhibitors of DNA or RNA synthesis (Schwartz, E. L. and Sartorelli, A. C. (1982) *Cancer Res.* 42: 2651-2655, Terada, M., Epner, E., Nudel, U., Salmon, J., Fibach, E., Rifkind, R. A., and Marks, P. A. (1978) *Proc. Natl. Acad. Sci.* (*USA*) 75: 2795-2799; Morin, M. J. and Sartorelli, A. C. (1984) *Cancer Res.* 44: 2807-2812; Schwartz, E. L., Brown, B. J., Nierenberg, M., Marsh, J. C., and Sartorelli, A. C. (1983) *Cancer Res.* 43: 2725-2730; Sugano, H., Furusawa, M., Kawaguchi, T., and Ikawa, Y. (1973) *Bibl. Hematol.* 39: 943-954; Ebert, P. S., Wars, I., and Buell, D. N. (1976) *Cancer Res.* 36: 1809-1813; Hayashi, M., Okabe, J., and Hozumi, M. (1979) *Gann* 70: 235-238).

Other inhibitors include DMPQ (5,7-dimethoxy-3-(4-pyridinyl)quinoline dihydrochloride), Aminogenistein (4'-amino-6-hydroxyflavone), Erbstatin analog (2,5-dihydroxymethylcinnamate, methyl 2,5-dihydroxycinnamate), Imatinib (Gleevec™, Glivec™; ST1-571; 4-[(4-methyl-1-piperazinyl)methyl]-N-[4-methyl-3-[[4-(3-pyridinyl)-2-yrimidinyl]amino]-phenyl]benzamide methanesulfonate), LFM-A13 (2-Cyano-N-(2,5-dibromophenyl)-3-hydroxy-2-butenamide), PD153035 (ZM 252868; 4-[(3-bromophenyl) amino]-6,7-dimethoxyquinoline hydrochloride), Piceatannol (trans-3,3',4,5'-tetrahydroxystilbene, 4-[(1E)-2-(3,5-dihydroxyphenyl)ethenyl]-1,2-benzenediol), PP1 (4-amino-5-(4-methylphenyl)-7-(t-butyl)pyrazolo[3,4-d]pyrimidine), PP2 (4-amino-5-(4-chlorophenyl)-7-(t-butyl)pyrazolo[3,4,d] pyrimidine), Pertuzumab (Omnitarg™; rhuMAb2C4), SU4312 (3-[[4-(dimethylamino) phenyl]methylene]-1,3-dihydro-2H-indol-2-one), SU6656 (2,3-dihydro-N,N-dimethyl-2-oxo-3-[(4,5,6,7-tetrahydro-1H-indol-2-yl)methylene]-1H-indole-5-sulfonamide), Bevacizumab (Avastin®; rhuMAb VEGF), Semaxanib (SU5416), SU6668 (Sugen, Inc.), and ZD6126 (Angiogene Pharmaceuticals).

Other agents may also be useful for use with the present invention, for example, for adjunct therapies. Such adjunctive agents can be used to enhance the effectiveness of anticancer agents or to prevent or treat conditions associated with anticancer agents such as low blood counts, neutropenia, anemia, hypersensitivity reactions, thrombocytopenia, hypercalcemia, mucositis, bruising, bleeding, toxicity (e.g., Leucovorin), fatigue, pain, nausea, and vomiting. Antiemetic agents (e.g., 5-HT receptor blockers or benzodiazepines), anti-inflammatory agents (e.g., adrenocortical steroids or antihistamines), and acid reducing agents (e.g., $H_2$ receptor blockers) can be useful for increasing patient tolerance to cancer therapy. Examples of $H_2$ receptor blockers include Ranitidine, Famotidine, and Cimetidine. Examples of antihistamines include Diphenhydramine, Clemastine, Chlorpheniramine, Chlorphenamine, Dimethindene maleate, and Promethazine. Examples of steroids include Dexamethasone, Hydrocortisone, and Prednisone. Other agents include growth factors such as epoetin alpha (e.g., Procrit®, Epogen®) for stimulating red blood cell production, G-CSF (granulocyte colony-stimulating factor; filgrastim, e.g., Neupogen®) for stimulating neutrophil production, GM-CSF (granulocyte-macrophage colony-stimulating factor) for stimulating production of several white blood cells, including macrophages, and IL-11 (interleukin-11, e.g., Neumega®) for stimulating production of platelets.

Leucovorin (e.g., Leucovorin calcium, Roxane Laboratories, Inc., Columbus, Ohio; also called folinic acid, calcium folinate, citrovorum factor) can be used as an antidote to folic acid antagonists, and can also potentiate the activity of certain drugs, such as Fluorouracil. Leucovorin calcium is the calcium salt of N-[4-[[(2-amino-5-formyl-1,4,5,6,7,8-hexahydro-4-oxo-6-pteridinyl)methyl]amino]benzoyl]-L-glutamic acid.

Dexamethasone (e.g., Decadron®; Merck & Co., Inc., Whitehouse Station, N.J.) is a synthetic adrenocortical steroid that can be used as an anti-inflammatory agent to control allergic reactions, e.g., drug hypersensitivity. Dexamethasone tablets for oral administration comprise 9-fluoro-11-beta,17,21-trihydroxy-16-alpha-methylpregna-1,4-diene-3,20-dione. Dexamethasone phosphate for intravenous administration comprises 9-fluoro-11β,17-dihydroxy-16α-methyl-21-(phosphonooxy)pregna-1,4-diene-3,20-dione disodium salt. Diphenhydramine (e.g., Benadryl®; Parkedale Pharmaceuticals, Inc., Rochester, Mich.) is an antihistamine drug used for amelioration of allergic reactions. Diphenhydramine hydrochloride (e.g., Diphenhydramine HCl for injection) is 2-(diphenylmethoxy)-N,N-dimethylethylamine hydrochloride. Ranitidine (e.g., Zantac®; GlaxoSmithKline, Research Triangle Park, N.C.) is a competitive inhibitor of histamine at histamine $H_2$-receptors, and can be used to reduce stomach acid. Ranitidine hydrochloride (e.g., tablets or injection) is N[2-[[[5-[(dimethylamino)methyl]-2-furanyl]methyl]thio]ethyl]-N'-methyl-2-nitro-1,1-ethenediamine, HCl. Cimetidine (e.g., Tagamet®; GlaxoSmithKline, Research Triangle Park, N.C.) is also a competitive inhibitor of histamine at histamine H2 receptors, and can be used to reduce stomach acid. Cimetidine is N"-cyano-N-methyl-N'-[2-[[(5-methyl-1H-imidazol-4-yl)methyl]thio]-ethyl]-guanidine. Aprepitant (e.g., EMEND®; Merck & Co., Inc.) is a substance P/neurokinin 1 (NK1) receptor antagonist and antiemetic. Aprepitant is 5-[[(2R,3S)-2-[(1R)-1-[3,5-bis(trifluoromethyl)phenyl]ethoxy]-3-(4-fluorophenyl)-4-morpholinyl]methyl]-1,2-dihydro-3H-1,2,4-triazol-3-one.

Ondansetron (e.g., Zofran®; GlaxoSmithKline, Research Triangle Park, N.C.) is a selective blocking agent of 5-HT3 serotonin receptor and antiemetic. Ondansetron hydrochloride (e.g., for injection) is (±)1,2,3,9-tetrahydro-9-methyl-3-[(2-methyl-1H-imidazol-1-yl)methyl]-4H-carbazol-4-one, monohydrochloride, dehydrate. Lorazepam (e.g., Lorazepam Injection; Baxter Healthcare Corp., Deerfield, Ill.), is a benzodiazepine with anticonvulsant effects. Lorazepam is 7-chloro-5(2-chlorophenyl)-1,3-dihydro-3-hydroxy-2H-1,4-benzodiazepin-2-one.

Kits

The invention also includes a CLRMARKER-detection reagent, e.g., nucleic acids that specifically identify one or more CLRMARKER nucleic acids by having homologous nucleic acid sequences, such as oligonucleotide sequences, complementary to a portion of the CLRMARKER nucleic acids or antibodies to proteins encoded by the CLRMARKER nucleic acids packaged together in the form of a kit. The kits of the present invention allow one of skill in the art to generate the reference and subject expression profiles disclosed herein. The kits of the invention can also be used to advantageously carry out any of the methods provided in this disclosure. The oligonucleotides can be fragments of the CLRMARKER genes. For example the oligonucleotides can be 200, 150, 100, 50, 25, or less nucleotides in length. The CLRMARKER-detection reagents can also comprise, inter alia, antibodies or fragments of antibodies, and aptamers. The kit may contain in separate containers a nucleic acid or antibody (either already bound to a solid matrix or packaged separately with reagents for binding them to the matrix), control formulations (positive and/or negative), and/or a detectable label. Instructions (e.g., written, tape, VCR, CD-ROM, etc.) for carrying out the assay detecting one or more CLRMARKERS of the invention may be included in the kit. The assay may for example be in the form of a Northern blot hybridization or a sandwich ELISA as known in the art. Alternatively, the kit can be in the form of a microarray as known in the art.

Diagnostic kits for carrying out the methods described herein are produced in a number of ways. Preferably, the kits of the present invention comprise a control (or reference) sample derived from a subject having normal glucose levels. Alternatively, the kits can comprise a control sample derived from a subject who has been diagnosed with or identified as suffering from colorectal cancer. In one embodiment, the diagnostic kit comprises (a) an antibody (e.g., fibrinogen αC domain peptide) conjugated to a solid support and (b) a second antibody of the invention conjugated to a detectable group. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. Alternatively, a test kit contains (a) an antibody of the invention, and (b) a specific binding partner for the antibody conjugated to a detectable group. The test kit may be packaged in any suitable manner, typically with all elements in a single container, optionally with a sheet of printed instructions for carrying out the test.

For example, CLRMARKER detection reagents can be immobilized on a solid matrix such as a porous strip to form at least one CLRMARKER detection site. The measurement or detection region of the porous strip may include a plurality of sites containing a nucleic acid. A test strip may also contain sites for negative and/or positive controls. Alternatively, control sites can be located on a separate strip from the test strip. Optionally, the different detection sites may contain different amounts of immobilized nucleic acids, e.g., a higher amount in the first detection site and lesser amounts in subsequent sites. Upon the addition of test sample, the number of sites displaying a detectable signal provides a quantitative indication of the amount of CLRMARKERS present in the sample. The detection sites may be configured in any suitably detectable shape and are typically in the shape of a bar or dot spanning the width of a test strip.

Alternatively, the kit contains a nucleic acid substrate array comprising one or more nucleic acid sequences. The nucleic acids on the array specifically identify one or more nucleic acid sequences represented by CLRMARKERS 1-51. In various embodiments, the expression of 2, 3, 4, 5, 6, 7, 8, 9, 10, 15, 20, 25, 30, 40, 50, or more of the CLRMARKERS 1-51 can be identified by virtue of binding to the array. The substrate array can be on, e.g., a solid substrate, e.g., a "chip" as described in U.S. Pat. No. 5,744,305. Alternatively, the substrate array can be a solution array, e.g., xMAP (Luminex, Austin, Tex.), Cyvera (Illumina, San Diego, Calif.), CellCard (Vitra Bioscience, Mountain View, Calif.) and Quantum Dots' Mosaic (Invitrogen, Carlsbad, Calif.).

The skilled artisan can routinely make antibodies, nucleic acid probes, e.g., oligonucleotides, aptamers, siRNAs, antisense oligonucleotides, against any of the CLRMARKERS in Table 1. Such techniques are well-known to those of ordinary skill in the art.

Exemplary Embodiments of the Invention

One embodiment of the invention comprises total RNA extraction using a standard commercially available kit such as the RNeasy Protect midi kit (Qiagen, Valencia, Calif.). Each RNA preparation may also include DNase I and proteinase K (Qiagen) treatment according to the manufacturer's instructions. Yield of total RNA can be determined by absorbance at 260 nmol/L. RNA integrity can be assessed by both 260/280 nmol/L ratios and agarose gel electrophoresis.

In another embodiment of this disclosure, 1 µg of total RNA from each sample can be reverse-transcribed into cDNA in a final volume of 20 microliter (µl) containing specific enzyme for reverse transcription such as 4 U of Omniscript reverse transcriptase (Qiagen) in the manufacturer's buffer, containing oligo's such as 0.5 mmol/L of each dNTP, containing RNAse inhibiting enzymes such as 10 U RNase inhibitor (Promega, Madison, Wis.), and containing oligonucleotides such as 1 µmol/L NVd(T)s (5'-TTTTTTTTTTTTTTTTTTTVN-3'; SEQ ID NO: 103). The reactions can take place at 37° C. for up to 12 hours and can be stored at −20° C. until further use.

In yet another embodiment of the present invention, real-time, quantitative PCR reactions can be performed using the Cyber-Green methodology or using any other system frequently used to achieve real-time quantitative PCR reactions, such as the Amplifluor Universal Detection system (Intergen, Purchase, N.Y.). A quantitative thermocycler such as iCycler (Bio-Rad, Richmond, Calif.) can be used. PCR primers can be designed using Primer3 software (available at http://www-genome.wi.mit.edu/genomesoftware/other/primer3.html) to specifically amplify, for example, between 177 and 237 bp of sequences corresponding to genes of interest in the same PCR conditions. If using Amplifluor Universal Detection system, then an additional forward primer can be used for each gene of interest that contains a Z-sequence (ACTGAACCTGAC-CGTACA; SEQ ID NO: 104) at the 5' end required for Uni-Primer annealing. If using the Amplifluor Universal Detection system kit, then a "sunrise" primer strategy can be used. The UniPrimer contains the same Z-sequence, labeled with a reporter (such as FAM, 6-carboxyfluorescein) at the 5'-end and a quencher dye (such as DABSYL, 4-(dimethylamine) azo benzene sulfonic acid) at the 3'-end of Z-sequence.

In another embodiment of the invention, the first round of multiplex quantitative PCR, where each 100 µl PCR reaction may contain 1 µl of cDNA or plasmid, 5 U of HotStarTaq DNA polymerase (Qiagen) in the manufacturer's buffer, 0.5 µM/L of each dNTP, and 2 µl of primer mixture. The primer mixture can comprise forward and reverse primers for all of the genes of interest related to solid tumors, at a final concentration of 10 µM/L each. The PCR program may comprise 15 minutes at 95° C. to activate the polymerase, followed by 15 cycles of 20 seconds of denaturation at 95° C., 20 seconds of annealing at 60° C., and 35 seconds of elongation at 72° C. A final step of elongation at 72° C. for 10 minutes can be performed. This round of PCR is considered preamplification only and does not involve real-time PCR. For the second round of multiplex quantitative PCR, each 50 µl real-time PCR reaction may contain 1 µl of first round multiplex quantitative PCR reaction, 2.5 U of Hot-StarTaq DNA polymerase (Qiagen) in the manufacturer's buffer, 0.5 mmol/L of each dNTP, 0.02 µmol/L forward primer, and 0.2 µmol/L reverse primer for one gene, and 0.2 µmol/L UniPrimer. No Uniprimer will be used if the Cyber-Green methodology is used. The PCR program may consist of 15 minutes at 95° C. to activate the polymerase, followed by 50 cycles of 20 seconds of denaturation at 95° C., 20 seconds of annealing at 60° C., and 35 seconds of elongation at 72° C. A final elongation step at 72° C. for 10 minutes can be performed.

Since the disclosed methods are quantitative, comparisons of the expression patterns at a quantitative level between a variety of different cell states or cell types can be achieved. In general, total RNA can be isolated from the target sample, such as peripheral blood, using any isolation procedure. This RNA can then be used to generate first strand copy DNA (cDNA) using any procedure, for example, using random primers, oligo-dT primers or random-oligo-dT primers which are oligo-dT primers coupled on the 3'-end to short stretches of specific sequence covering all possible combinations, so the primer anneals at the junction between the polyA tract and non-polyA tract associated with messenger RNA (mRNA). The cDNA can then be used as a template in a PCR reaction. This PCR reaction is performed with primer pairs having sequences related to genes implicated in cancer that are specific for the expressed genes to be monitored. This reaction can contain as many different primer pairs related to cancer as desired, but typically includes between 5 and 100 different sets of primers, each specific for a single gene related to cancer or single isoform related to cancer (including any specific number between 5 and 100). Typically all of the primers will be present in equimolar concentrations. After performing a number of PCR cycles, for example, 15 cycles, such that the DNA would amplify at about greater than 80% or 85% or 90% or 95% of the doubling rate, the reactions are stopped. Typically, in the first round of PCR, if quantitative PCR (real time PCR) is performed, the threshold cycle of amplification would not be achieved.

The PCR reaction can then partitioned into new reaction tubes for a (new) additional round of PCR. Each of the tubes contains a fraction of the previous PCR reaction mixture which contains all of the products synthesized from all of the specific primers present in the first PCR mixture. In the second PCR mixture, which contains a fraction from the first PCR mixture, typically only one specific primer pair or a new primer pair is added, in addition to the universal primer having a sequence corresponding to the molecular beacon.

This second round of PCR can be performed using quantitative real time PCR protocols, which for example, rely on increases in fluorescence at each amplification cycle of the reaction (for example, probes that hybridize to a portion of one of the amplification probes) via the release of fluorescence from a quencher sequence, while the uniprimer (universal primer) is bound to the DNA sequence. Fluorescence approaches used in real-time quantitative PCR are typically based on a fluorescent reporter dye such as SYBR green, FAM, fluorescein, HEX, TET, TAMRA, etc. and a quencher such as DABSYL, Black Hole, etc. When the quencher is separated from the probe during the extension phase of PCR, the fluorescence of the reporter can be measured. Systems like Molecular Beacons, Taqman Probes, Scorpion Primers or Sunrise Primers and others use this approach to perform real-time quantitative PCR. Standard curves can be used in the disclosed methods, but other methods to derive absolute copy number of targets, such as analysis using C (t) can also be used.

Clinically, the two criteria that are important for assessing the effectiveness of biomarkers are sensitivity and specificity. Sensitivity of a biomarker defined clinically refers to percentage of subjects correctly diagnosed. Specificity of a biomarker in a clinical context is defined as the probability that the disease is detected at a curable stage. Ideally, biomarkers would have 100% clinical selectivity and 100% clinical sensitivity.

One embodiment of the present invention is a profile of candidate peripheral blood surrogate biomarkers preferably with sensitivity equal or above to 70% and specificity equal or above 95% required for managing subject care for solid tumors. As shown in Table 1, entries 1 to 51 are candidate polynucleotide coding sequences of peripheral blood surrogate biomarkers for solid tumors such as colorectal cancer, and include the name, entry number, forward primer, reverse primer and amplicon size for each gene product of interest.

Fluorescence intensity can generally be measured during the annealing step or alternatively, during the elongation step of each cycle. Threshold cycles (CT) for each reaction can be analyzed using iCycler software (BioRad). All real-time PCR experiments can be performed in triplicate and the average CT for triplicate experiments are used in all subsequent analyses. Reactions omitting enzyme or template must be used as negative controls. All reactions can be resolved by 1% agarose gel electrophoresis to confirm PCR amplification of specific genes in the profile. The amount of transcripts can be calculated by reference to respective standard curves.

The proposed method for analyzing and using a biomarker profile for solid tumors is to a) extract RNA from peripheral blood, b) reverse-transcribe said RNA into cDNA, c) perform a first round of PCR containing equimolar concentration of primers for said biomarkers, d) perform a second quantitative round of PCR specific for each biomarker of interest and e) perform statistical data analysis derived from disclosed composition and methods, using (for example) Principal Component Analysis (PCA).

By way of example and not intended to limit any aspect of the present invention, other compositions and methods that can be applied for analyzing data derived from the determination of the presence of one or more biomarkers of the present invention.

By way of example, other methods that can be used for analyzing data obtained by methods according to the present invention may involve any other method of quantification known in the art of nucleic acids to assess copy number, such as but not limited to amplification of specific sequences, oligonucleotide probes, hybridization of target genes with complementary probes, fragmentation by restriction endonucleases and study of the resulting fragments (polymorphisms), pulsed field gels techniques, isothermic multiple-displacement amplification, rolling circle amplification or replication, immuno-PCR, among others known to those skilled in the art.

Other methods that can be used for analyzing said biomarkers on solid tumors involves any other art-recognized statistical analyses of results, such as gene clustering, data mining tools, and other algorithms or computed indices known in the art and disclosed herein.

EXAMPLES

Example 1

Data Analysis for Detection of Colorectal Adenomas and Carcinomas

The statistical analyses were based on quantification of 51 species of RNA. Species handling, analysis and quantification was performed by scqmRT-PCR methodology and transformed in copy number per standardized mass of input RNA using calibration curves (see Therianos et al., (2004) Am. J. Pathol. 164(3): 795-806, and PCT/US02/38806, the contents of which are expressly incorporated herein by reference).

There are four classes (biological conditions) of samples called controls (CON), inflammatory bowel diseases (IBD), advanced polyps/adenomas (POL) and carcinomas (CAR), which are stages I-II of colorectal cancer. Table 1 shows the number of samples derived from each of the four classes of biological conditions.

TABLE 1

| Biological conditions | |
|---|---|
| Class | Number |
| CON | 51 |
| IBD | 26 |
| POL | 32 |
| CAR | 23 |

In particular, the following pairwise class discrimination problems are of interest:

TABLE 2

| Pairwise class discrimination studied | | | |
|---|---|---|---|
| Pb NB | Class 0 | Class 1 | N(total) |
| 1 | CON | POL and CAR | 106 |
| 2 | CON | POL | 83 |
| 3 | CON | CAR | 74 |
| 4 | CON and IBD | POL and CAR | 132 |

Biostatistical Methods—Data Pre-Processing and Classification

Copy number data 'x' were transformed to a log-abundance measure defined as $y=\log(1+x)$. This algorithm was used throughout the analyses discussed herein. For classification, 'y' is standardized by subtraction of the median and division by the interquartile range (IQR) of the relevant sample set, for example, the current training set in cross-validation loops.

The classifier used here is a variant of the compound covariate predictor (CCP) described by John Tukey, (1993) Controlled Clinical Trials, and popularized in the microarray field by Richard Simons work. It is based on a weighted averaging log expression levels, where weights can be for example the values of the t-statistic between the classes being studied. This classifier is based on an independent feature model, also called a "naive classifier" in the literature, since the independence assumption is strong and almost always wrong. The advantage of such a model is that it is less prone to overfitting and therefore to failure in validation, when the sample sizes available for training are small and insufficient for a good estimation of the relation between variables. Mis-parametrization of a non-naive model leads to failure in validation. The classification function is based on scoring the samples by weighted averaging over the genes included in the classifier. The standardized log-abundance measure is used for gene selection and sample scoring. Feature selection takes the top genes ranked by the absolute difference of the medians after standardization. The weights are proportional to the (signed) difference of the medians. In cross-validation, the multi-gene scores in each loop are re-standardized by subtraction of the median and division by the interquartile range (IQR) of the current training set of samples.

Discrimination ability is quantified by the AUC, as the primary statistical endpoint, the area under the ROC curve. A random classifier has a curve stochastically fluctuating around the $y=x$ line and an expected AUC of 0.5. Alternatively, the equivalent plot of sensitivity and specificity is drawn here, where it might be easier to read off these two quantities. Confidence intervals for the AUC are computed by the bias-reduced bootstrap case cross-validation (BR-BCCV) method of Jiang, Varma and Simon, 2008.

Results—Class Discrimination Ability of Single Genes

Figure 2:
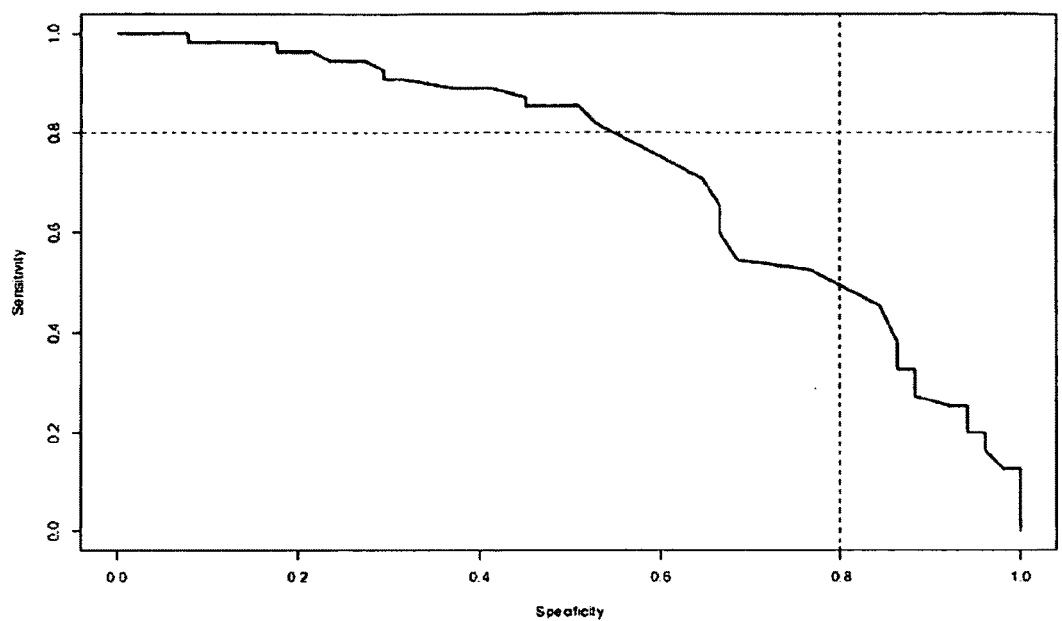
FIG. 2 is a class discrimination ability of single gene ROC curve for the CLRMARKER ESM1 as compared between CON vs. POL and CAR groups.

In FIGS. 1A-1E, we plotted the sensitivity and specificity for the top gene over the range of possible cutoffs. Since we selected the best performing of 51 genes, the performance estimation is positively biased, and represents an upper limit for the discrimination that can be reached with one single marker for this problem in this dataset. It is also illustrative of the relation between AUC values and sensitivity and specificity values. AUC is a measure of average discrimination over all possible cutoffs and is well defined. Between sensitivity and specificity, there is a trade-off that is cutoff-dependent, such that there is no unique determination of their values without a further specification and the concentration on only one point of the ROC curve. Cross-validation is used for a more unbiased estimation of class discrimination performance. Confidence intervals for performance indicators for these single gene predictors could be estimated here by bootstrapping over samples. Table 3 represents a comparison of CON vs. POL and CAR, and shows the top 20 performing genes by AUC, raw p-values from a Wilcoxon test for equality of medians between the two groups, adjusted p-values as determined by Hochberg's method for family-wise correction and false discovery rates as determined by the Benjamini-Hochberg method. FIG. 2 is a graphical representative of a ROC curve measuring the levels of a CLRMARKER, ESM1 in groups CON vs. POL and CAR.

TABLE 3

Top 20 genes as calculated by AUC, raw p-values from a Wilcoxon test for equality of medians between the two groups, adjusted p-values (Hochberg's method for family-wise correction) and false discovery rate (by the Benjamini-Hochberg method.

| geneNB | gene names | AUC | sign | p-value | H. adj p-value | BH FDR |
|---|---|---|---|---|---|---|
| 8 | ESM1 | 0.7278 | −1 | 1e−04 | 0.0051 | 0.0051 |
| 2 | sGC | 0.7071 | −1 | 2e−04 | 0.01 | 0.0051 |
| 28 | DKK1 | 0.6882 | 1 | 8e−04 | 0.0392 | 0.0119 |
| 6 | VEGFA | 0.6824 | −1 | 0.0012 | 0.0576 | 0.0119 |
| 24 | ANG2 | 0.6818 | −1 | 0.0013 | 0.0611 | 0.0119 |
| 10 | CYP51 | 0.6802 | −1 | 0.0014 | 0.0644 | 0.0119 |
| 20 | MMP9 | 0.659 | −1 | 0.0048 | 0.216 | 0.035 |
| 7 | LTF | 0.6487 | −1 | 0.0084 | 0.3696 | 0.0535 |
| 50 | HPRT | 0.6455 | −1 | 0.0098 | 0.4214 | 0.0555 |
| 29 | MMP7 | 0.6387 | 1 | 0.0139 | 0.5838 | 0.0709 |
| 21 | BIRC4 | 0.6342 | −1 | 0.0172 | 0.7052 | 0.0797 |
| 5 | APQ1 | 0.6312 | −1 | 0.0199 | 0.796 | 0.0846 |
| 33 | CAD5 | 0.6291 | −1 | 0.022 | 0.858 | 0.0863 |
| 36 | INTB3 | 0.6207 | 1 | 0.0323 | 0.9899 | 0.1122 |
| 38 | CK19 | 0.6194 | 1 | 0.0341 | 0.9899 | 0.1122 |
| 39 | CK20 | 0.6187 | 1 | 0.0352 | 0.9899 | 0.1122 |
| 45 | BANK1 | 0.6148 | 1 | 0.0417 | 0.9899 | 0.1198 |
| 37 | CEA | 0.6144 | 1 | 0.0423 | 0.9899 | 0.1198 |
| 12 | CXCL10 | 0.6105 | −1 | 0.0499 | 0.9899 | 0.1339 |
| 16 | ADAMTS1 | 0.6093 | −1 | 0.0526 | 0.9899 | 0.1341 |

TABLE 4

Figure 3:
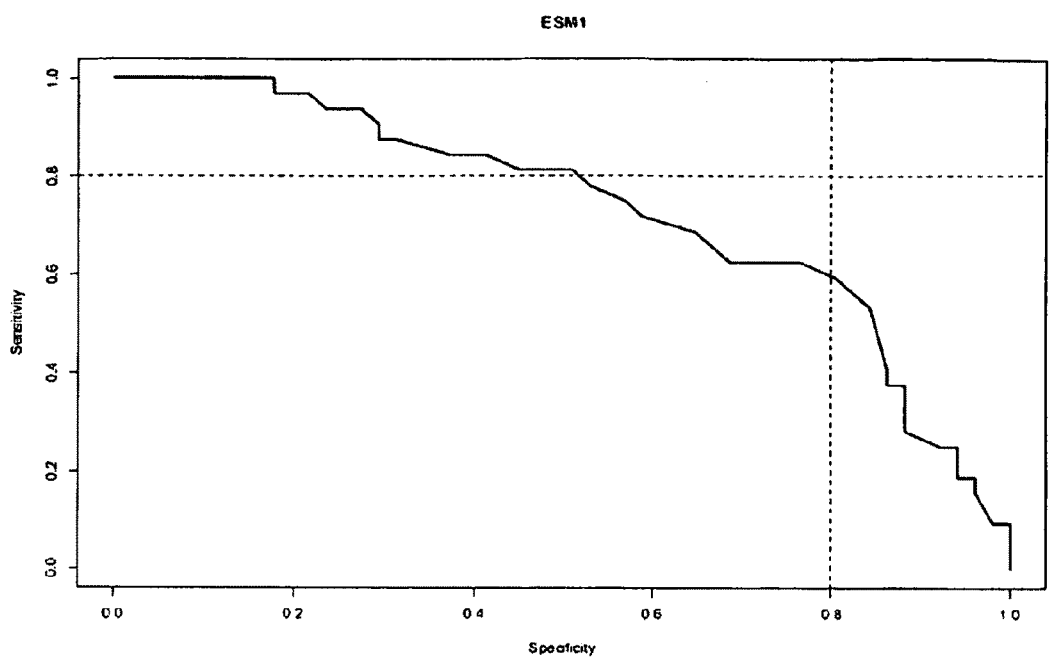
FIG. 3 is a class discrimination ability of single gene ROC curve for the CLRMARKER ESM1 as compared between CON and POL groups.

CON vs. POL; Top 20 genes by AUC, raw p-values from a Wilcoxon test for equality of medians between the two groups, adjusted p-values (Hochberg's method for family-wise correction) and false discovery rate (by the Benjamini-Hochberg method). FIG. 3 shows the ROC curve for ESM1 as between the groups CON vs. POL.

| geneNB | gene names | AUC | sign | p-value | H. adj p-value | BH FDR |
|---|---|---|---|---|---|---|
| 8 | ESM1 | 0.731 | −1 | 4e−04 | 0.0204 | 0.0204 |
| 16 | ADAMTS 1 | 0.6991 | −1 | 0.0024 | 0.12 | 0.0612 |
| 24 | ANG2 | 0.685 | −1 | 0.0047 | 0.2303 | 0.0657 |
| 2 | sGC | 0.6817 | −1 | 0.0055 | 0.264 | 0.0657 |
| 28 | DKK1 | 0.6743 | 1 | 0.0078 | 0.3666 | 0.0657 |
| 36 | INTB3 | 0.6716 | 1 | 0.0088 | 0.4048 | 0.0657 |
| 6 | VEGFA | 0.6697 | −1 | 0.0095 | 0.4275 | 0.0657 |
| 15 | LPC2 | 0.6679 | 1 | 0.0103 | 0.4532 | 0.0657 |
| 10 | CYP51 | 0.6618 | −1 | 0.0135 | 0.5805 | 0.0765 |
| 38 | CK19 | 0.6581 | 1 | 0.0158 | 0.6636 | 0.0806 |
| 50 | HPRT | 0.6547 | −1 | 0.0181 | 0.7421 | 0.0839 |
| 45 | BANK1 | 0.6501 | 1 | 0.0218 | 0.872 | 0.0879 |
| 32 | CYP2S1 | 0.6495 | 1 | 0.0224 | 0.8736 | 0.0879 |
| 29 | MMP7 | 0.6468 | 1 | 0.025 | 0.95 | 0.0911 |
| 27 | CCL8 | 0.6419 | −1 | 0.0302 | 0.9963 | 0.1027 |
| 46 | FRDM3 | 0.6369 | 1 | 0.0365 | 0.9963 | 0.1163 |
| 20 | MMP9 | 0.6293 | −1 | 0.0483 | 0.9963 | 0.1449 |
| 37 | CEA | 0.6271 | 1 | 0.0522 | 0.9963 | 0.1479 |
| 49 | B2M | 0.6232 | −1 | 0.0598 | 0.9963 | 0.1605 |
| 33 | CAD5 | 0.6164 | −1 | 0.0754 | 0.9963 | 0.1923 |

TABLE 5

Figure 4:
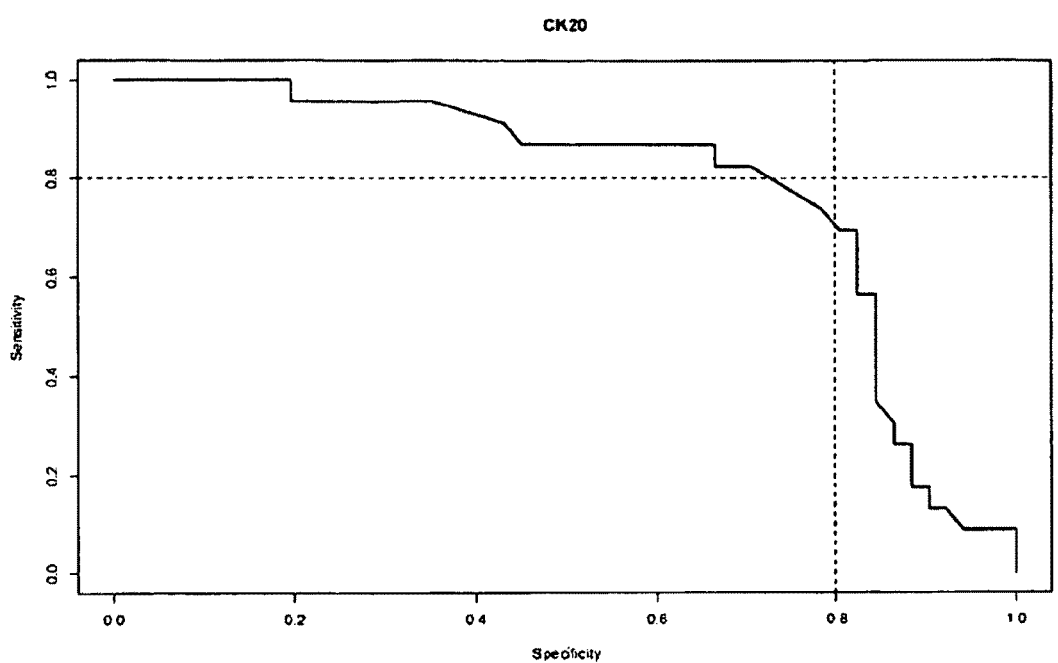
FIG. 4 is a class discrimination ability of single gene ROC curve for the CLRMARKER CK20 as compared between CON and CAR groups.
Figure 5:
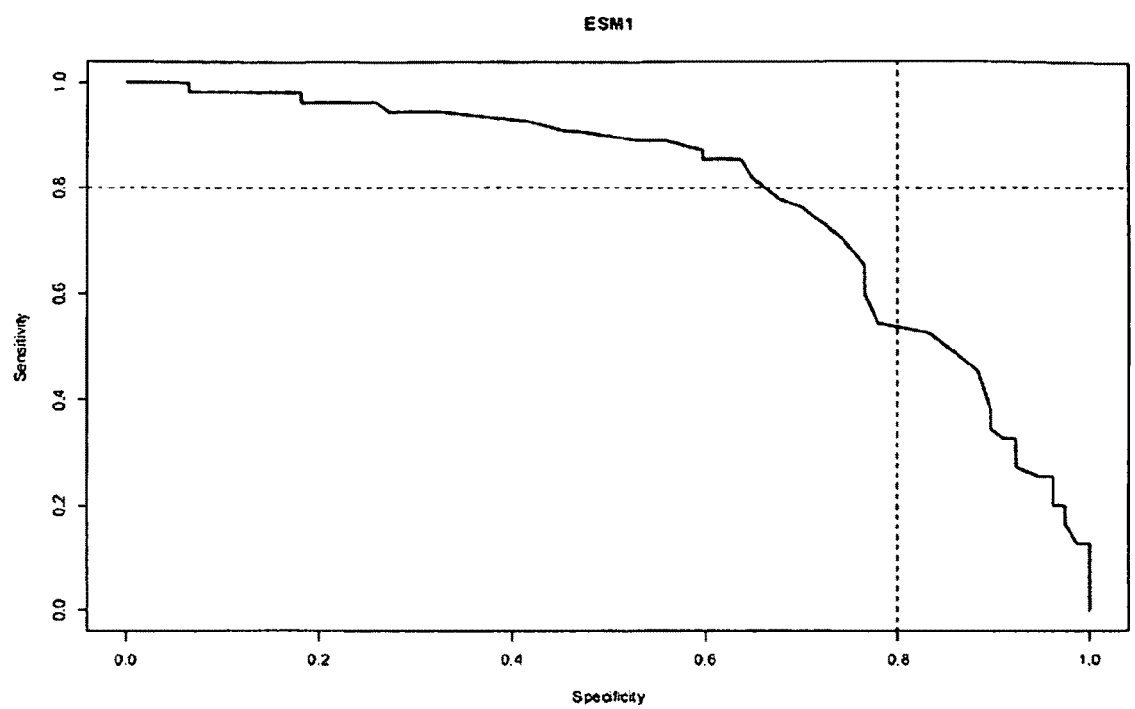
FIG. 5 is a class discrimination ability of single gene ROC curve for the CLRMARKER ESM1 as compared between Con and IBD vs. POL and CAR groups.
Figure 6:
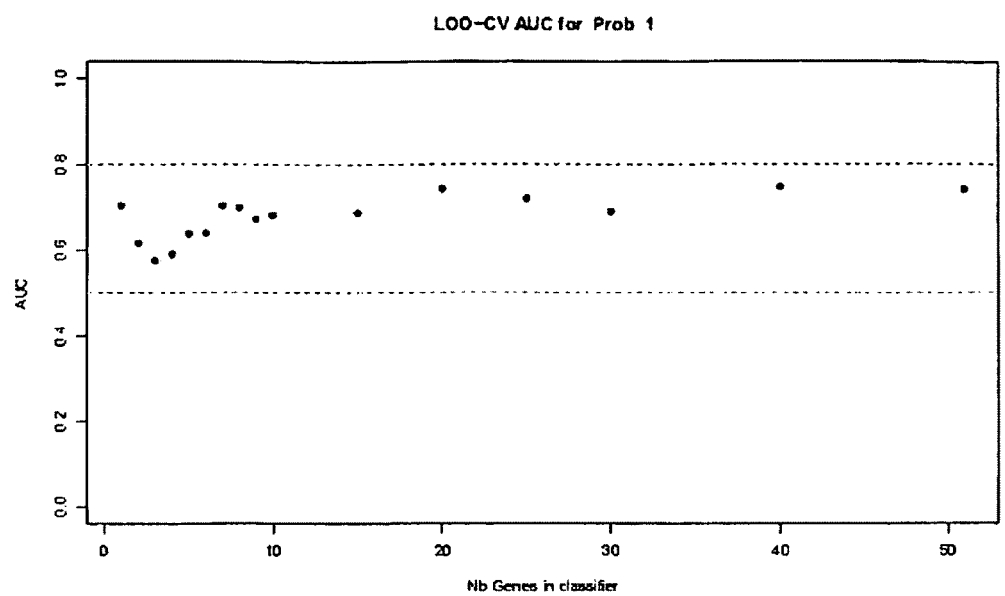
FIG. 6 depicts the class discrimination ability of multigene classifiers area under the curve and the number of genes in a "leave one out" cross-validation model of CON vs. POL and CAR.
Figure 7:
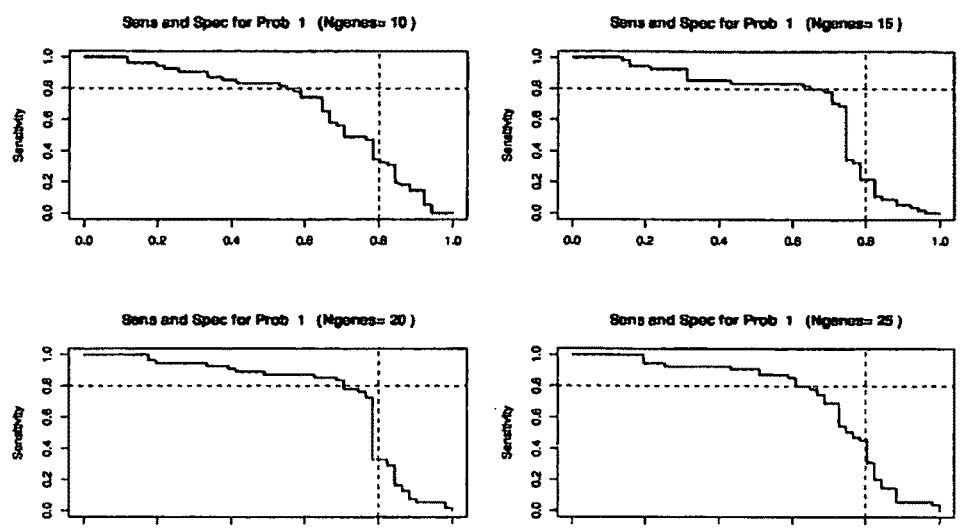
FIG. 7 depicts graphical representations of sensitivity and specificity for four of the LOOCV iterations described in the Examples for CON vs. POL and CAR.
Figure 8:
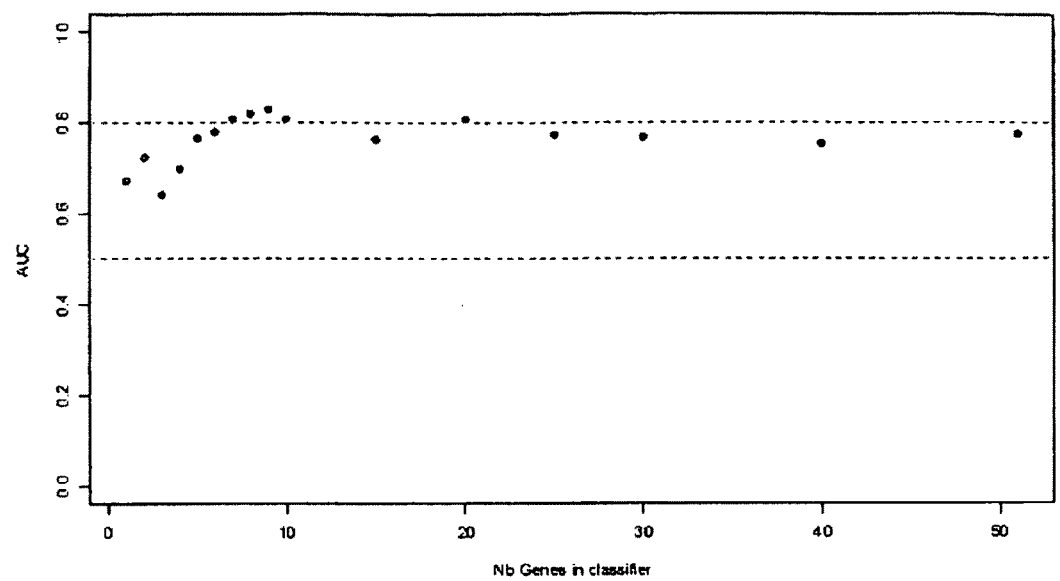
FIG. 8 depicts the class discrimination ability of multigene classifiers area under the curve and the number of genes in a "leave one out" cross-validation model of CON vs. POL.
Figure 9:
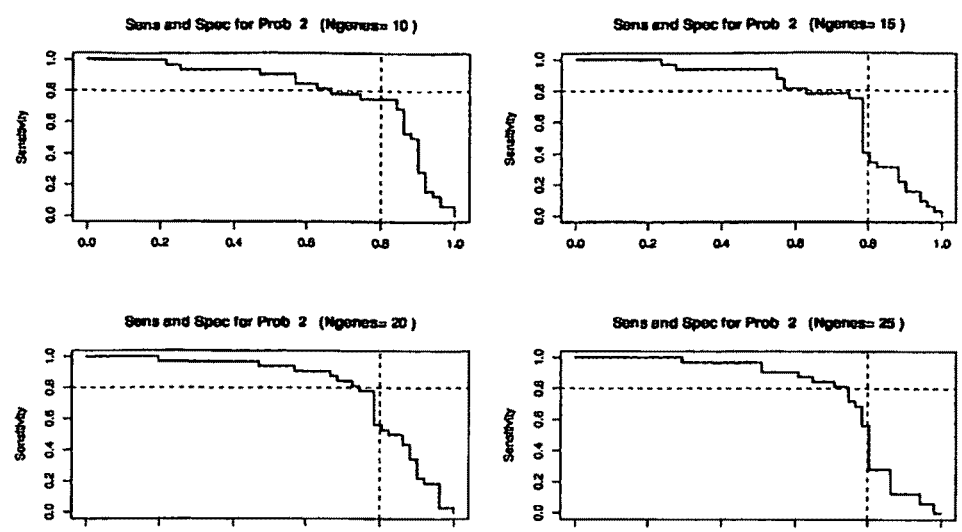
FIG. 9 depicts graphical representations of sensitivity and specificity for four of the LOOCV iterations described in the Examples for CON vs. POL.
Figure 10:
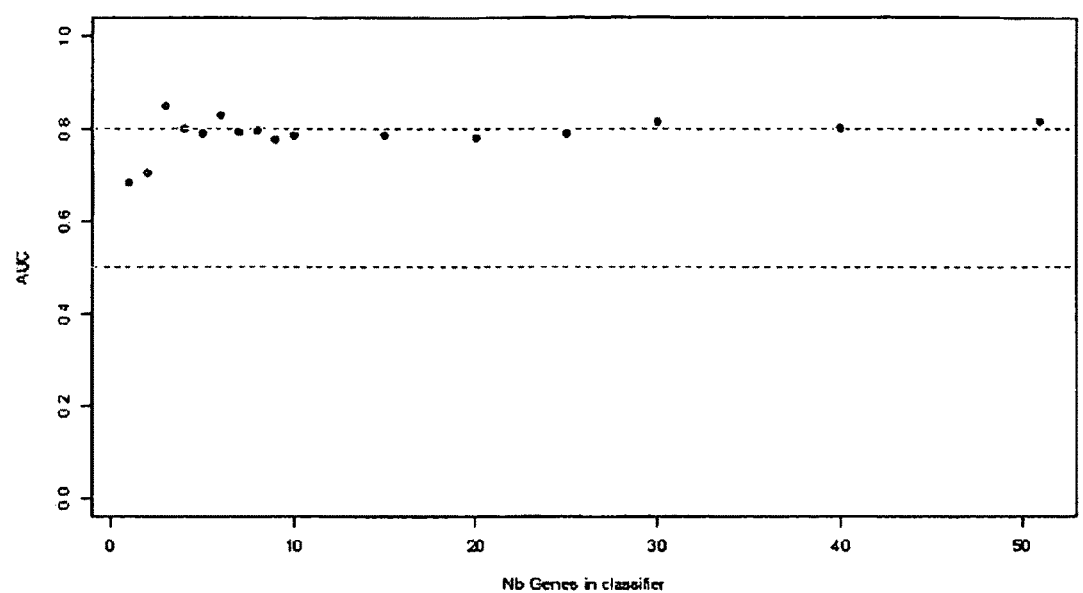
FIG. 10 depicts the class discrimination ability of multigene classifiers area under the curve and the number of genes in a "leave one out" cross-validation model of CON vs. CAR.
Figure 11:
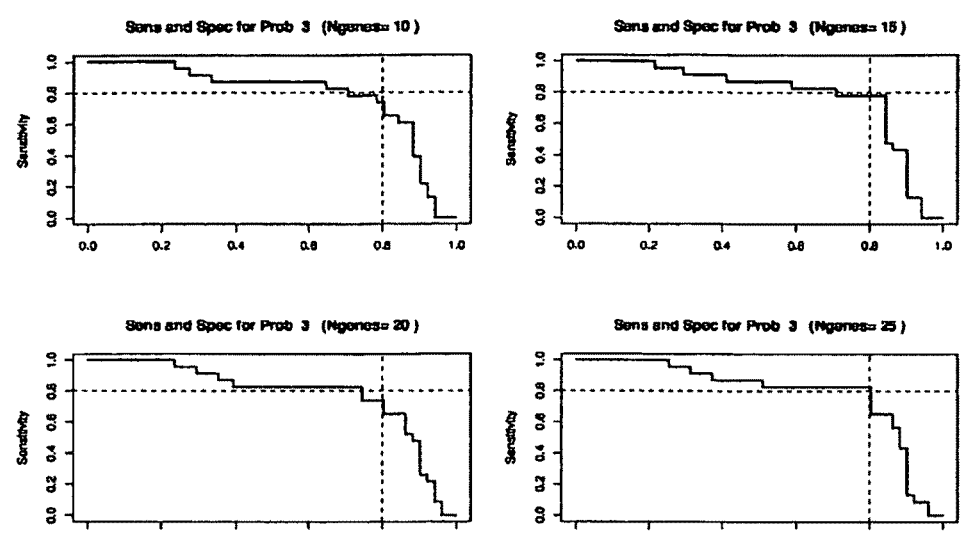
FIG. 11 depicts graphical representations of sensitivity and specificity for four of the LOOCV iterations described in the Examples for CON vs. CAR.
Figure 12:
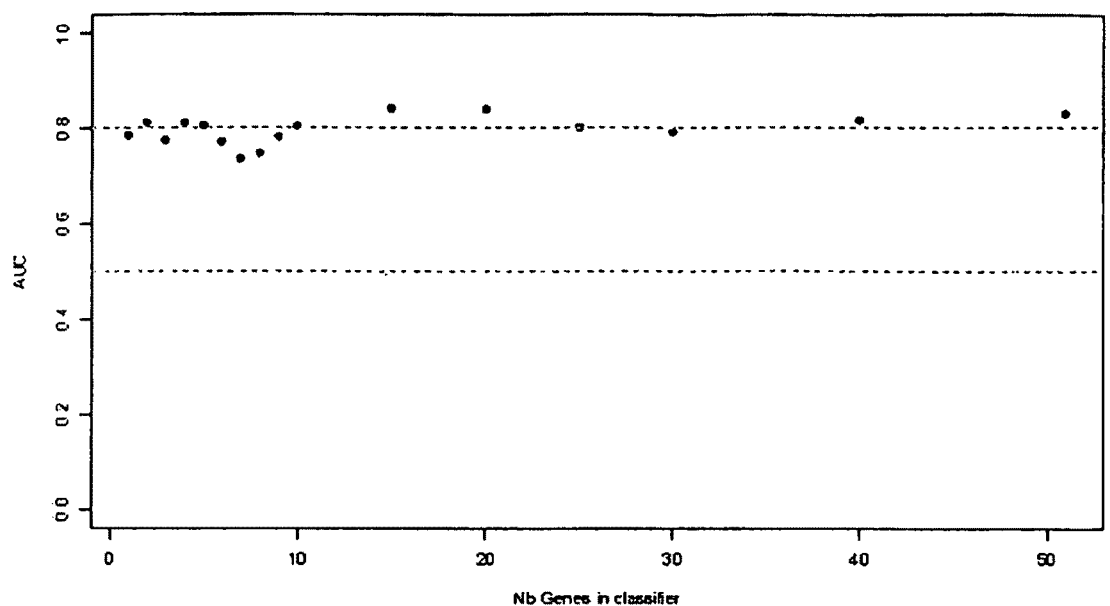
FIG. 12 depicts the class discrimination ability of multigene classifiers area under the curve and the number of genes in a "leave one out" cross-validation model of CON and IBD vs. POL and CAR.
Figure 13:
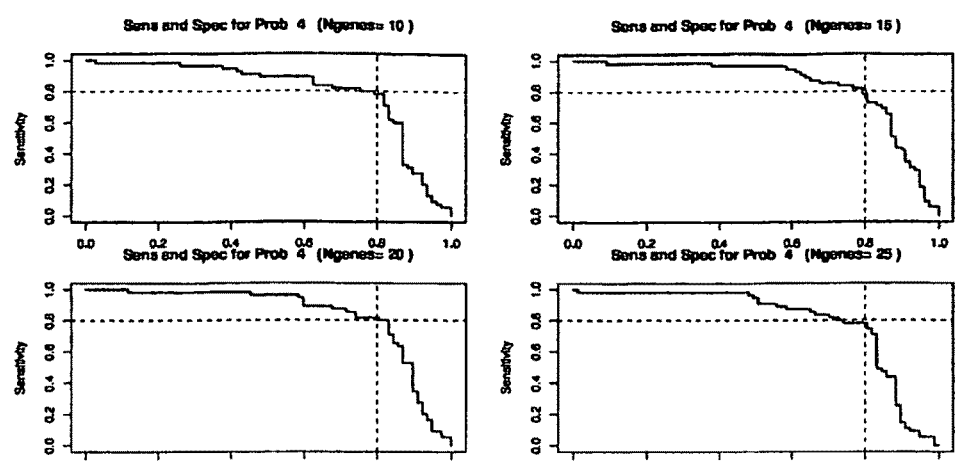
FIG. 13 depicts graphical representations of sensitivity and specificity for four of the LOOCV iterations described in the Examples for CON and IBD vs. POL and CAR.
Figure 14:
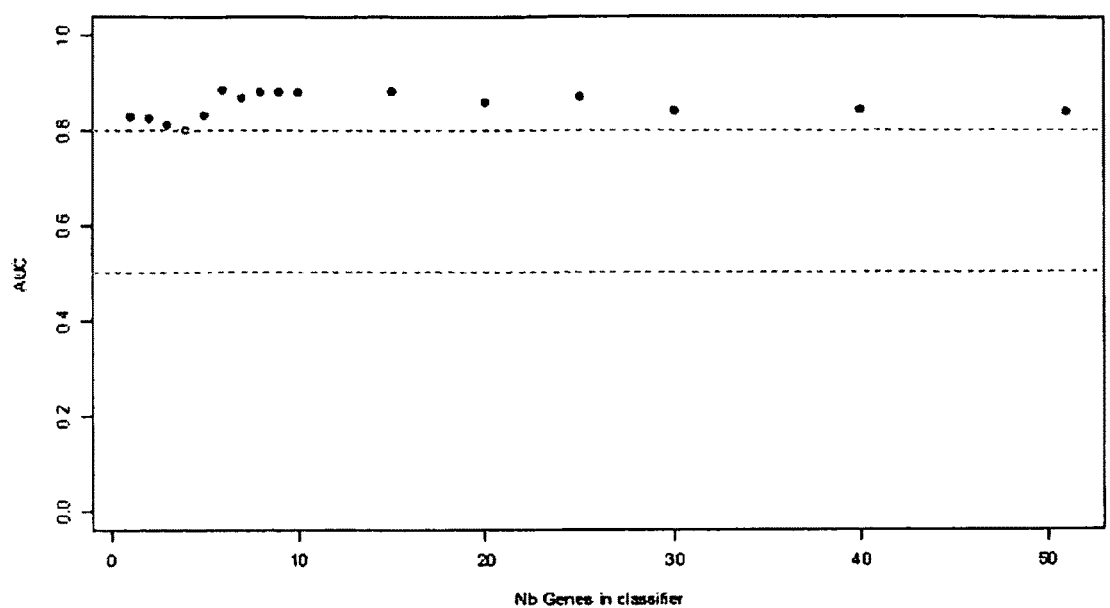
FIG. 14 depicts the class discrimination ability of multigene classifiers area under the curve and the number of genes in a "leave one out" cross-validation model for CON vs. IBD.
Figure 15:
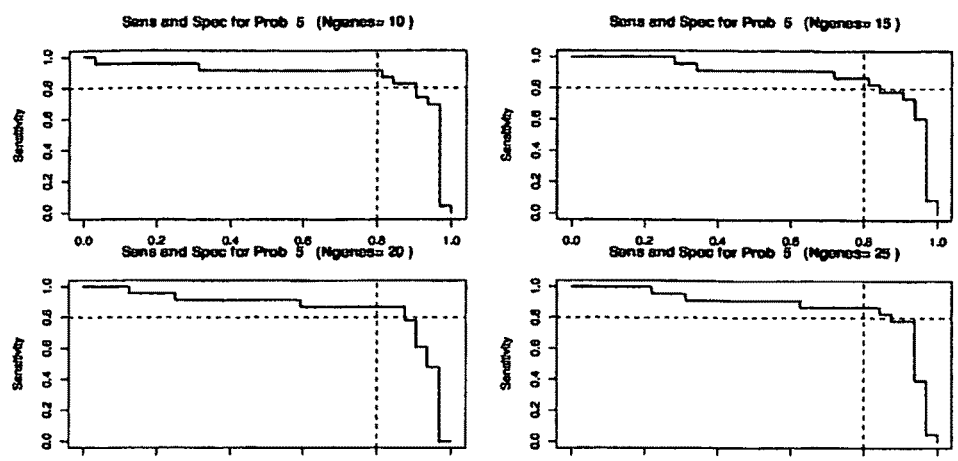
FIG. 15 depicts graphical representations of sensitivity and specificity for four of the LOOCV iterations described in the Examples for CON vs. IBD

CON vs. CAR; Top 20 genes by AUC, raw p-values from a Wilcoxon test for equality of medians between the two groups, adjusted p-values (Hochberg's method for family-wise correction) and false discovery rate (by the Benjamini-Hochberg method). FIG. 4 shows a ROC curve for CLRMARKER CK20.

| geneNB | gene names | AUC | sign | p-value | H. adj p-value | BH FDR |
|---|---|---|---|---|---|---|
| 39 | CK20 | 0.7818 | 1 | 1e−04 | 0.0051 | 0.0051 |
| 7 | LTF | 0.7536 | −1 | 5e−04 | 0.025 | 0.0128 |
| 2 | sGC | 0.7425 | −1 | 9e−04 | 0.0441 | 0.0153 |
| 48 | GAPDH | 0.7332 | −1 | 0.0014 | 0.0672 | 0.0178 |
| 15 | LPC2 | 0.7242 | −1 | 0.0021 | 0.0987 | 0.0187 |
| 8 | ESM1 | 0.7234 | −1 | 0.0022 | 0.1012 | 0.0187 |
| 28 | DKK1 | 0.7076 | 1 | 0.0044 | 0.198 | 0.0237 |
| 10 | CYP51 | 0.7059 | −1 | 0.0048 | 0.2064 | 0.0237 |
| 31 | ECAD | 0.7059 | −1 | 0.0048 | 0.2064 | 0.0237 |
| 25 | TIE2 | 0.7016 | −1 | 0.0057 | 0.2394 | 0.0237 |
| 20 | MMP9 | 0.7003 | −1 | 0.006 | 0.244 | 0.0237 |
| 6 | VEGFA | 0.6999 | −1 | 0.0061 | 0.244 | 0.0237 |
| 21 | BIRC4 | 0.6991 | −1 | 0.0064 | 0.247 | 0.0237 |
| 12 | CXCL10 | 0.6986 | −1 | 0.0065 | 0.247 | 0.0237 |
| 34 | INTB5 | 0.6969 | −1 | 0.007 | 0.259 | 0.0238 |
| 9 | EPST1 | 0.691 | −1 | 0.0089 | 0.3204 | 0.0284 |
| 14 | VCAM1 | 0.6807 | −1 | 0.0132 | 0.462 | 0.0396 |
| 24 | ANG2 | 0.6773 | −1 | 0.0151 | 0.5134 | 0.0428 |
| 5 | APQ1 | 0.6756 | −1 | 0.0161 | 0.5313 | 0.0432 |
| 46 | FRDM3 | 0.6726 | −1 | 0.018 | 0.576 | 0.0459 |

TABLE 6

CON and IBD vs. POL and CAR; Top 20 genes by AUC, raw p-values from a Wilcoxon test for equality of medians between the two groups, adjusted p-values (Hochberg's method for family-wise correction) and false discovery rate (by the Benjamini-Hochberg method).

| geneNB | gene names | AUC | sign | p-value | H. adj p-value | BH FDR |
|---|---|---|---|---|---|---|
| 8 | ESM1 | 0.7875 | −1 | 0 | 0 | 0 |
| 24 | ANG2 | 0.7349 | −1 | 0 | 0 | 0 |
| 33 | CAD5 | 0.6999 | −1 | 1e−04 | 0.0049 | 0.0017 |
| 2 | sGC | 0.6812 | −1 | 4e−04 | 0.0192 | 0.0051 |
| 16 | ADAMTS 1 | 0.6766 | −1 | 6e−04 | 0.0282 | 0.0051 |
| 22 | NTN4 | 0.6732 | −1 | 7e−04 | 0.0315 | 0.0051 |
| 37 | CEA | 0.6726 | 1 | 7e−04 | 0.0315 | 0.0051 |

TABLE 6-continued

CON and IBD vs. POL and CAR; Top 20 genes by AUC, raw p-values from a Wilcoxon test for equality of medians between the two groups, adjusted p-values (Hochberg's method for family-wise correction) and false discovery rate (by the Benjamini-Hochberg method).

| geneNB | gene names | AUC | sign | p-value | H. adj p-value | BH FDR |
|---|---|---|---|---|---|---|
| 41 | KLK6 | 0.6706 | −1 | 9e−04 | 0.0387 | 0.0051 |
| 28 | DKK1 | 0.6698 | 1 | 9e−04 | 0.0387 | 0.0051 |
| 29 | MMP7 | 0.6542 | 1 | 0.0026 | 0.1066 | 0.0121 |
| 36 | INTB3 | 0.6541 | 1 | 0.0026 | 0.1066 | 0.0121 |
| 38 | CK19 | 0.6433 | 1 | 0.0051 | 0.204 | 0.0217 |
| 3 | s100A9 | 0.64 | 1 | 0.0062 | 0.2418 | 0.0243 |
| 20 | MMP9 | 0.6336 | −1 | 0.009 | 0.342 | 0.0328 |
| 50 | HPRT | 0.6286 | −1 | 0.012 | 0.444 | 0.0398 |
| 11 | THBS1 | 0.6279 | 1 | 0.0125 | 0.45 | 0.0398 |
| 25 | TIE2 | 0.6146 | −1 | 0.0251 | 0.8785 | 0.0734 |
| 9 | EPST1 | 0.614 | −1 | 0.0259 | 0.8806 | 0.0734 |
| 7 | LTF | 0.6104 | −1 | 0.0311 | 0.9283 | 0.0835 |
| 21 | BIRC4 | 0.6083 | −1 | 0.0344 | 0.9283 | 0.0877 |

Optimal Choice of Genes and AUC

We attempted to estimate the prediction performance that can be expected with the available data. Compared to the single gene analysis, the features to be used for a predictor must be chosen before knowing the outcome. This situation is simulated by using leave-one-out (LOO) cross-validation (CV).

In turn, we took out each sample from the data and automatically constructed a classifier (a scoring function) that makes no use whatsoever of any information about the sample that has been excluded. The scoring function was then applied to the left out sample. This was repeated for each sample to generate a full set of scores. Then, classification performance was computed on this set of scores. Each sample is scored with a newly constructed (and therefore different) classifier that can make use of a different set of genes. The method delivers unbiased estimation of the performance that can be expected on new data by generating a unique classifier based on the full dataset. It corrects for the bias that is present when features of the classifier are chosen based on information of the samples that are also used for testing the performance of a classifier.

The results of LOOCV for a specific choice of the classification algorithm are presented in graphical form in FIGS. 13-16.

A number of models and the number of genes used by the classifier were tested by varying only one parameter. This number F was fixed in each LOOCV run, but different numbers were used to determine if the discrimination can be improved by using information from multiple genes. The genes selected were the top-n according to a ranking statistics, wherein the ranking depends only on the training set, not on F, so models with different F are positively correlated. Variability of performance over F represents differences between models with different numbers of genes but also chance variation and sources of instability in the modeling. The degree of multiplicity remains limited and choice of the best performing F for the next step was not expected to introduce an appreciable amount of bias. For models with a number of genes between 10 and 25, plots of sensitivity and specificity were added. See, for example, FIGS. 13-16.

Table 7 is a summary of LOOCV-estimated AUC values obtained from the analyses described herein and in FIGS. 13-16.

| model | NB of genes | Pb1 | Pb2 | Pb3 | Pb4 |
|---|---|---|---|---|---|
| 1 | 1 | 0.705 | 0.672 | 0.685 | 0.787 |
| 2 | 2 | 0.618 | 0.724 | 0.706 | 0.814 |
| 3 | 3 | 0.576 | 0.641 | 0.850 | 0.777 |
| 4 | 4 | 0.592 | 0.699 | 0.801 | 0.813 |
| 5 | 5 | 0.639 | 0.766 | 0.790 | 0.808 |
| 6 | 6 | 0.640 | 0.780 | 0.831 | 0.774 |
| 7 | 7 | 0.705 | 0.809 | 0.794 | 0.737 |
| 8 | 8 | 0.701 | 0.822 | 0.798 | 0.749 |
| 9 | 9 | 0.674 | 0.831 | 0.778 | 0.784 |
| 10 | 10 | 0.683 | 0.808 | 0.788 | 0.806 |
| 11 | 15 | 0.688 | 0.764 | 0.788 | 0.843 |
| 12 | 20 | 0.744 | 0.809 | 0.783 | 0.842 |
| 13 | 25 | 0.721 | 0.775 | 0.791 | 0.804 |
| 14 | 30 | 0.692 | 0.769 | 0.817 | 0.795 |
| 15 | 40 | 0.749 | 0.754 | 0.803 | 0.818 |
| 16 | 51 | 0.742 | 0.776 | 0.818 | 0.832 |

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the present disclosure.

What is claimed is:

1. A method of diagnosing or identifying colorectal cancer in a subject, comprising:
   a. measuring an effective amount of nucleic acid of CLRMARKERS comprising CXCL10, INTB5, and ADAMTS1 in a blood sample from the subject;
   b. comparing the amount to a reference value, wherein an increase or decrease in the amount of nucleic acid of the CLRMARKERS comprising CXCL10, INTB5, and ADAMTS1 relative to the reference value indicates that the subject suffers from colorectal cancer; and
   c. administering to the subject at least one colorectal-modulating agent when the subject suffers from colorectal cancer identified by step b.

2. The method of claim 1, wherein the reference value comprises an index value, a value derived from one or more colorectal cancer risk prediction algorithms or computed indices, a value derived from a subject not suffering from colorectal cancer, or a value derived from a subject diagnosed with or identified as suffering from colorectal cancer.

3. The method according to claim 1, wherein the subject comprises one who has been previously diagnosed as having colorectal cancer, one who has not been previously diagnosed as having colorectal cancer, or one who is asymptomatic for the colorectal cancer.

* * * * *